United States Patent [19]

Hashino et al.

[11] Patent Number: 5,475,100
[45] Date of Patent: Dec. 12, 1995

[54] ARTIFICIAL ANTIBODY

[75] Inventors: Kimikazu Hashino, Takatsuki; Fusao Kimizuka, Ohmihachiman; Ikunoshin Kato, Uji; Yoshikazu Kurosawa, Nagoya; Koiti Titani, Kasugai; Kiyotoshi Sekiguchi, Sakai, all of Japan

[73] Assignees: Fujita Health University; Takara Shuzo Co., Ltd., both of Japan

[21] Appl. No.: 109,106

[22] Filed: Aug. 19, 1993

Related U.S. Application Data

[63] Continuation of Ser. No. 725,668, Jul. 3, 1991, abandoned.

[30] Foreign Application Priority Data

Jul. 13, 1990 [JP] Japan ................................. 2-184158
Jun. 7, 1991 [JP] Japan ................................. 3-162521

[51] Int. Cl.⁶ ............................ C07H 21/00; C07K 16/00
[52] U.S. Cl. ................... 536/23.53; 536/23.1; 536/23.5; 530/387.3
[58] Field of Search .............................. 536/23.1, 23.53

[56] References Cited

U.S. PATENT DOCUMENTS 4,614,517  9/1986  Ruoslahti .
4,816,567  3/1989  Cabilly et al. .

FOREIGN PATENT DOCUMENTS 9014103  11/1990  WIPO .

OTHER PUBLICATIONS

Kameyana et al FEBS LETTS 244(2): 301–306 (Feb. 1989).
Maeda et al J.B.C. 264(26): 15165, 1989.
Symons et al Molecular Immunology 26(9):841, 1989.

*Primary Examiner*—Suzanne E. Ziska
*Attorney, Agent, or Firm*—Wenderoth, Lind & Ponack

[57] ABSTRACT

This invention provides an antibody having antigen binding activity and which has a heavy chain constant region into which has been introduced an RGDS amino acid sequence giving the antibody affinity for cells, including macrophages. The antibody exhibits artificial cell adhesive activity which is the newly expressed activity that results from insertion of the RGDS amino acid sequence. This antibody having artificial cell adhesive activity can accelerate the phagocytosis of macrophages, and can activate other effector cells. Therefore, this antibody contributes to the self-defense mechanism.

2 Claims, 8 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:

( A ) NAME/KEY:
                        ( B ) LOCATION:
                        ( C ) IDENTIFICATION METHOD:
                        ( D ) OTHER INFORMATION:

( x ) PUBLICATION INFORMATION:
                        ( A ) AUTHORS:
                        ( B ) TITLE:
                        ( C ) JOURNAL:
                        ( D ) VOLUME:
                        ( E ) ISSUE:
                        ( F ) PAGES:
                        ( G ) DATE:
                        ( H ) DOCUMENT NUMBER:
                        ( I ) FILING DATE:
                        ( J ) PUBLICATION DATE:
                        ( K ) RELEVANT RESIDUES IN SEQ ID NO:

( x i ) SEQUENCE DESCRIPTION: SEQ ID NO:1:

Arg Gly Asp Ser
 1

( 2 ) INFORMATION FOR SEQ ID NO:2:

( i ) SEQUENCE CHARACTERISTICS:
                        ( A ) LENGTH: 5 amino acids
                        ( B ) TYPE: amino acid
                        ( C ) STRANDEDNESS: single
                        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
                        ( A ) ORGANISM:
                        ( B ) STRAIN:
                        ( C ) INDIVIDUAL ISOLATE:
                        ( D ) DEVELOPMENTAL STAGE:
                        ( E ) HAPLOTYPE:
                        ( F ) TISSUE TYPE:
                        ( G ) CELL TYPE:
                        ( H ) CELL LINE:
                        ( I ) ORGANELLE:

( v i i ) IMMEDIATE SOURCE:
                        ( A ) LIBRARY:
                        ( B ) CLONE:

( v i i i ) POSITION IN GENOME:
                        ( A ) CHROMOSOME/SEGMENT:
                        ( B ) MAP POSITION:
                        ( C ) UNITS:

( i x ) FEATURE:
                        ( A ) NAME/KEY:
                        ( B ) LOCATION:
                        ( C ) IDENTIFICATION METHOD:
                        ( D ) OTHER INFORMATION:

( x ) PUBLICATION INFORMATION:
                        ( A ) AUTHORS:
                        ( B ) TITLE:
                        ( C ) JOURNAL:
                        ( D ) VOLUME:
                        ( E ) ISSUE:
                        ( F ) PAGES:
                        ( G ) DATE:
                        ( H ) DOCUMENT NUMBER:
                        ( I ) FILING DATE:
                        ( J ) PUBLICATION DATE:
                        ( K ) RELEVANT RESIDUES IN SEQ ID NO:

(x i) SEQUENCE DESCRIPTION: SEQ ID NO:2:

Tyr  Ile  Gly  Ser  Arg
 1                    5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (i i i) HYPOTHETICAL:

(i v) ANTI-SENSE:

(v) FRAGMENT TYPE:

(v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY:
        (B) CLONE:

(v i i i) POSITION IN GENOME:
        (A) CHROMOSOME/SEGMENT:
        (B) MAP POSITION:
        (C) UNITS:

(i x) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(x i) SEQUENCE DESCRIPTION: SEQ ID NO:3:

Glu  Ile  Leu  Asp  Val
 1                    5

(2) INFORMATION FOR SEQ ID NO:4:

(i) SEQUENCE CHARACTERISTICS:
        (A) LENGTH: 1980 base pairs
        (B) TYPE: nucleic acid
        (C) STRANDEDNESS: double
        (D) TOPOLOGY: linear (i i) MOLECULE TYPE: Genomic DNA (i i i) HYPOTHETICAL:

( i v ) ANTI-SENSE:

( v ) FRAGMENT TYPE:

( v i ) ORIGINAL SOURCE:
   ( A ) ORGANISM:
   ( B ) STRAIN:
   ( C ) INDIVIDUAL ISOLATE:
   ( D ) DEVELOPMENTAL STAGE:
   ( E ) HAPLOTYPE:
   ( F ) TISSUE TYPE:
   ( G ) CELL TYPE:
   ( H ) CELL LINE:
   ( I ) ORGANELLE:

( v i i ) IMMEDIATE SOURCE:
   ( A ) LIBRARY:
   ( B ) CLONE:

( v i i i ) POSITION IN GENOME:
   ( A ) CHROMOSOME/SEGMENT:
   ( B ) MAP POSITION:
   ( C ) UNITS:

( i x ) FEATURE:
   ( A ) NAME/KEY:
   ( B ) LOCATION: 1-208
   ( C ) IDENTIFICATION METHOD:
   ( D ) OTHER INFORMATION: /note="E intron 1;"

( i x ) FEATURE:
   ( A ) NAME/KEY:
   ( B ) LOCATION: 209-502
   ( C ) IDENTIFICATION METHOD:
   ( D ) OTHER INFORMATION: /note="E CDS;"

( i x ) FEATURE:
   ( A ) NAME/KEY:
   ( B ) LOCATION: 503-890
   ( C ) IDENTIFICATION METHOD:
   ( D ) OTHER INFORMATION: /note="E intron 2;"

( i x ) FEATURE:
   ( A ) NAME/KEY:
   ( B ) LOCATION: 891-935
   ( C ) IDENTIFICATION METHOD:
   ( D ) OTHER INFORMATION: /note="E CDS;"

( i x ) FEATURE:
   ( A ) NAME/KEY:
   ( B ) LOCATION: 936-1053
   ( C ) IDENTIFICATION METHOD:
   ( D ) OTHER INFORMATION: /note="E intron 3;"

( i x ) FEATURE:
   ( A ) NAME/KEY:
   ( B ) LOCATION: 1054-1383
   ( C ) IDENTIFICATION METHOD:
   ( D ) OTHER INFORMATION: /note="E CDS;"

( i x ) FEATURE:
   ( A ) NAME/KEY:
   ( B ) LOCATION: 1384-1479
   ( C ) IDENTIFICATION METHOD:
   ( D ) OTHER INFORMATION: /note="E intron 4;"

( i x ) FEATURE:
   ( A ) NAME/KEY:
   ( B ) LOCATION: 1480-1821
   ( C ) IDENTIFICATION METHOD:
   ( D ) OTHER INFORMATION: /note="E CDS;"

( i x ) FEATURE:
   ( A ) NAME/KEY:
   ( B ) LOCATION: 1923-1929
   ( C ) IDENTIFICATION METHOD:
   ( D ) OTHER INFORMATION: /note="E poly A signal"

( x ) PUBLICATION INFORMATION:

( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:4:

```
AGCTTTCTGG GGCAGGCCAG GCCTGACCTT GGCTTTGGGG CAGGGAGGGG GCTAAGGTGA        60

GGCAGGTGGC GCCAGCAGGT GCACACCCAA TGCCCATGAG CCCAGACACT GGACGCTGAA       120

CCTCGCGGAC AGTTAAGAAC CCAGGGGCCT CTGCGCCTGG GCCCAGCTCT GTCCCACACC       180

GCGGTCACAT GGCACCACCT CTCTTGCA GCC TCC ACC AAG GGC CCA TCG GTC          232
                                Ala Ser Thr Lys Gly Pro Ser Val
                                 1               5

TTC CCC CTG GCA CCC TCC TCC AAG AGC ACC TCT GGG GGC ACA GCG             277
Phe Pro Leu Ala Pro Ser Ser Lys Ser Thr Ser Gly Gly Thr Ala
         10              15                  20

GCC CTG GGC TGC CTG GTC AAG GAC TAC TTC CCC GAA CCG GTG ACG             322
Ala Leu Gly Cys Leu Val Lys Asp Tyr Phe Pro Glu Pro Val Thr
     25              30                  35

GTG TCG TGG AAC TCA GGC GCC CTG ACC AGC GGC GTG CAC ACC TTC             367
Val Ser Trp Asn Ser Gly Ala Leu Thr Ser Gly Val His Thr Phe
 40                  45                  50

CCG GCT GTC CTA CAG TCC TCA GGA CTC TAC TCC CTC AGC AGC GTG             412
Pro Ala Val Leu Gln Ser Ser Gly Leu Tyr Ser Leu Ser Ser Val
 55                  60                  65

GTG ACC GTG CCC TCC AGC AGC TTG GGC ACC CAG ACC TAC ATC TGC             457
Val Thr Val Pro Ser Ser Ser Leu Gly Thr Gln Thr Tyr Ile Cys
         70              75                  80

AAC GTG AAT CAC AAG CCC AGC AAC ACC AAG GTG GAC AAG AAA GTT             502
Asn Val Asn His Lys Pro Ser Asn Thr Lys Val Asp Lys Lys Val
         85              90                  95

GGTGAGAGGC CAGCACAGGG AGGGAGGGTG TCTGCTGGAA GCAGGCTCAG CGCTCCTGCC       562

TGGACGCATC CCGGCTATGC AGCCCCAGTC CAGGGCAGCA AGGCAGGCCC CGTCTGCCTC       622

TTCACCCGGA GCCTCTGCCC GCCCCACTCA TGCTCAGGGA GAGGGTCTTC TGGCTTTTTC       682

CCAGGCTCTG GGCAGGCACA GGCTAGGTGC CCCTAACCCA GGCCCTGCAC ACAAGGGGC        742

AGGTGCTGGG CTCAGACCTG CCAAGAGCCA TATCCGGGAG GACCCTGCCC CTGACCTAAG       802

CCCACCCCAA AGGCCAAACT CTCCACTCCC TCAGCTCGGA CACCTTCTCT CCTCCCAGAT       862

TCCAGTAACT CCCAATCTTC TCTCTGCA GAG CCC AAA TCT TGT GAC AAA ACT         914
                                Glu Pro Lys Ser Cys Asp Lys Thr
                                 1               5

CAC ACA TGC CCA CCG TGC CCA GGTAAGCCAG CCCAGGCCTC GCCCTCCAGC            965
His Thr Cys Pro Pro Cys Pro
         10              15

TCAAGGCGGG ACAGGTGCCC TAGAGTAGCC TGCATCCAGG GACAGGCCCC AGCCGGGTGC      1025

TGACACGTCC ACCTCCATCT CTTCCTCA GCA CCT GAA CTC CTG GGG GGA CCG        1077
                                Ala Pro Glu Leu Leu Gly Gly Pro
                                 1               5

TCA GTC TTC CTC TTC CCC CCA AAA CCC AAG GAC ACC CTC ATG ATC            1122
Ser Val Phe Leu Phe Pro Pro Lys Pro Lys Asp Thr Leu Met Ile
         10              15                  20

TCC CGG ACC CCT GAG GTC ACA TGC GTG GTG GTG GAC GTG AGC CAC            1167
```

-continued

```
Ser Arg Thr Pro Glu Val Thr Cys Val Val Val Asp Val Ser His
    25              30                  35

GAA GAC CCT GAG GTC AAG TTC AAC TGG TAC GTG GAC GGC GTG GAG         1212
Glu Asp Pro Glu Val Lys Phe Asn Trp Tyr Val Asp Gly Val Glu
    40              45                  50

GTG CAT AAT GCC AAG ACA AAG CCG CGG GAG GAG CAG TAC AAC AGC         1257
Val His Asn Ala Lys Thr Lys Pro Arg Glu Glu Gln Tyr Asn Ser
    55              60                  65

ACG TAC CGG GTG GTC AGC GTC CTC ACC GTC CTG CAC CAG GAC TGG         1302
Thr Tyr Arg Val Val Ser Val Leu Thr Val Leu His Gln Asp Trp
    70              75                  80

CTG AAT GGC AAG GAG TAC AAG TGC AAG GTC TCC AAC AAA GCC CTC         1347
Leu Asn Gly Lys Glu Tyr Lys Cys Lys Val Ser Asn Lys Ala Leu
    85              90                  95

CCA GCC CCC ATC GAG AAA ACC ATC TCC AAA GCC AAA GGTGGGACCC          1393
Pro Ala Pro Ile Glu Lys Thr Ile Ser Lys Ala Lys
    100             105             110

GTGGGGTGCG AGGGCCACAT GGACAGAGGC CGGCTCGGCC CACCCTCTGC CCTGAGAGTG   1453

ACCGCTGTAC CAACCTCTGT CCTACA GGG CAG CCC CGA GAA CCA CAG GTG TAC   1506
                              Gly Gln Pro Arg Glu Pro Gln Val Tyr
                                1                   5

ACC CTG CCC CCA TCC CGG GAT GAG CTG ACC AAG AAC CAG GTC AGC         1551
Thr Leu Pro Pro Ser Arg Asp Glu Leu Thr Lys Asn Gln Val Ser
10              15                  20

CTG ACC TGC CTG GTC AAA GGC TTC TAT CCC AGC GAC ATC GCC GTG         1596
Leu Thr Cys Leu Val Lys Gly Phe Tyr Pro Ser Asp Ile Ala Val
    25              30                  35

GAG TGG GAG AGC AAT GGG CAG CCG GAG AAC AAC TAC AAG ACC ACG         1641
Glu Trp Glu Ser Asn Gly Gln Pro Glu Asn Asn Tyr Lys Thr Thr
    40              45                  50

CCT CCC GTG CTG GAC TCC GAC GGC TCC TTC TTC CTC TAC AGC AAG         1686
Pro Pro Val Leu Asp Ser Asp Gly Ser Phe Phe Leu Tyr Ser Lys
    55              60                  65

CTC ACC GTG GAC AAG AGC ACC GGC CGG GGC GAC AGC CCT AGG TGG         1731
Leu Thr Val Asp Lys Ser Thr Gly Arg Gly Asp Ser Pro Arg Trp
    70              75                  80

CAG CAG GGG AAC GTC TTC TCA TGC TCC GTG ATG CAT GAG GCT CTG         1776
Gln Gln Gly Asn Val Phe Ser Cys Ser Val Met His Glu Ala Leu
    85              90                  95

CAC AAC CAC TAC ACG CAG AAG AGC CTC TCC CTG TCT CCG GGT AAA         1821
His Asn His Tyr Thr Gln Lys Ser Leu Ser Leu Ser Pro Gly Lys
100             105                 110

TGAGTGCGAC GGCCGGCAAG CCCCGCTCCC CGGGCTCTCG CGGTCGCACG AGGATGCTTG   1881

GCACGTACCC CCTGTACATA CTTCCCGGGC GCCCAGCATG GAAATAAAGC ACCCAGCGCT   1941

GCCCTGGGCC CCTGCGAGAC TGTGATGGTT CTTTCCACG                          1980
```

( 2 ) INFORMATION FOR SEQ ID NO:5:

( i ) SEQUENCE CHARACTERISTICS:
        ( A ) LENGTH: 2009 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION: 1-208
    ( C ) IDENTIFICATION METHOD:
    ( D ) OTHER INFORMATION: /note="E intron 1;"

( i x ) FEATURE:
    ( A ) NAME/KEY:
    ( B ) LOCATION: 209-502
    ( C ) IDENTIFICATION METHOD:
    ( D ) OTHER INFORMATION: /note="E CDS;"

( i x ) FEATURE:
    ( A ) NAME/KEY:
    ( B ) LOCATION: 503-890
    ( C ) IDENTIFICATION METHOD:
    ( D ) OTHER INFORMATION: /note="E intron 2;"

( i x ) FEATURE:
    ( A ) NAME/KEY:
    ( B ) LOCATION: 891-935
    ( C ) IDENTIFICATION METHOD:
    ( D ) OTHER INFORMATION: /note="E CDS;"

( i x ) FEATURE:
    ( A ) NAME/KEY:
    ( B ) LOCATION: 936-1053
    ( C ) IDENTIFICATION METHOD:
    ( D ) OTHER INFORMATION: /note="E intron 3;"

( i x ) FEATURE:
    ( A ) NAME/KEY:
    ( B ) LOCATION: 1054-1383
    ( C ) IDENTIFICATION METHOD:
    ( D ) OTHER INFORMATION: /note="E CDS;"

( i x ) FEATURE:
    ( A ) NAME/KEY:
    ( B ) LOCATION: 1384-1479
    ( C ) IDENTIFICATION METHOD:
    ( D ) OTHER INFORMATION: /note="E intron 4;"

( i x ) FEATURE:
    ( A ) NAME/KEY:
    ( B ) LOCATION: 1480-1800
    ( C ) IDENTIFICATION METHOD:
    ( D ) OTHER INFORMATION: /note="E CDS;"

( i x ) FEATURE:
    ( A ) NAME/KEY:
    ( B ) LOCATION: 1902-1908
    ( C ) IDENTIFICATION METHOD:
    ( D ) OTHER INFORMATION: /note="E poly A signal"

( x ) PUBLICATION INFORMATION:
    ( A ) AUTHORS:
    ( B ) TITLE:
    ( C ) JOURNAL:

-continued

```
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:5:

AGCTTTCTGG  GGCAGGCCAG  GCCTGACCTT  GGCTTTGGGG  CAGGGAGGGG  GCTAAGGTGA         60

GGCAGGTGGC  GCCAGCAGGT  GCACACCCAA  TGCCCATGAG  CCCAGACACT  GGACGCTGAA        120

CCTCGCGGAC  AGTTAAGAAC  CCAGGGGCCT  CTGCGCCTGG  GCCCAGCTCT  GTCCCACACC        180

GCGGTCACAT  GGCACCACCT  CTCTTGCA GCC TCC ACC AAG GGC CCA TCG GTC              232
                                Ala Ser Thr Lys Gly Pro Ser Val
                                 1               5

TTC CCC CTG GCA CCC TCC TCC AAG AGC ACC TCT GGG GGC ACA GCG                   277
Phe Pro Leu Ala Pro Ser Ser Lys Ser Thr Ser Gly Gly Thr Ala
         10              15                  20

GCC CTG GGC TGC CTG GTC AAG GAC TAC TTC CCC GAA CCG GTG ACG                   322
Ala Leu Gly Cys Leu Val Lys Asp Tyr Phe Pro Glu Pro Val Thr
     25              30                  35

GTG TCG TGG AAC TCA GGC GCC CTG ACC AGC GGC GTG CAC ACC TTC                   367
Val Ser Trp Asn Ser Gly Ala Leu Thr Ser Gly Val His Thr Phe
 40              45                  50

CCG GCT GTC CTA CAG TCC TCA GGA CTC TAC TCC CTC AGC AGC GTG                   412
Pro Ala Val Leu Gln Ser Ser Gly Leu Tyr Ser Leu Ser Ser Val
     55              60                  65

GTG ACC GTG CCC TCC AGC AGC TTG GGC ACC CAG ACC TAC ATC TGC                   457
Val Thr Val Pro Ser Ser Ser Leu Gly Thr Gln Thr Tyr Ile Cys
 70              75                  80

AAC GTG AAT CAC AAG CCC AGC AAC ACC AAG GTG GAC AAG AAA GTT                   502
Asn Val Asn His Lys Pro Ser Asn Thr Lys Val Asp Lys Lys Val
     85              90                  95

GGTGAGAGGC  CAGCACAGGG  AGGGAGGGTG  TCTGCTGGAA  GCAGGCTCAG  CGCTCCTGCC        562

TGGACGCATC  CCGGCTATGC  AGCCCCAGTC  CAGGGCAGCA  AGGCAGGCCC  CGTCTGCCTC        622

TTCACCCGGA  GCCTCTGCCC  GCCCCACTCA  TGCTCAGGGA  GAGGGTCTTC  TGGCTTTTTC        682

CCAGGCTCTG  GGCAGGCACA  GGCTAGGTGC  CCCTAACCCA  GGCCCTGCAC  ACAAAGGGGC        742

AGGTGCTGGG  CTCAGACCTG  CCAAGAGCCA  TATCCGGGAG  GACCCTGCCC  CTGACCTAAG        802

CCCACCCCAA  AGGCCAAACT  CTCCACTCCC  TCAGCTCGGA  CACCTTCTCT  CCTCCCAGAT        862

TCCAGTAACT  CCCAATCTTC  TCTCTGCA GAG CCA AAA TCT TGT GAC AAA ACT              914
                                Glu Pro Lys Ser Cys Asp Lys Thr
                                 1               5

CAC ACA TGC CCA CCG TGC CCA GGTAAGCCAG  CCCAGGCCTC  GCCCTCCAGC                965
His Thr Cys Pro Pro Cys Pro
         10              15

TCAAGGCGGG  ACAGGTGCCC  TAGAGTAGCC  TGCATCCAGG  GACAGGCCCC  AGCCGGGTGC       1025

TGACACGTCC  ACCTCCATCT  CTTCCTCA GCA CCT GAA CTC CTG GGG GGA CCG             1077
                                Ala Pro Glu Leu Leu Gly Gly Pro
                                 1               5

TCA GTC TTC CTC TTC CCC CCA AAA CCC AAG GAC ACC CTC ATG ATC                  1122
Ser Val Phe Leu Phe Pro Pro Lys Pro Lys Asp Thr Leu Met Ile
         10              15                  20

TCC CGG ACC CCT GAG GTC ACA TGC GTG GTG GTG GAC GTG AGC CAC                  1167
Ser Arg Thr Pro Glu Val Thr Cys Val Val Val Asp Val Ser His
     25              30                  35
```

```
GAA GAC CCT GAG GTC AAG TTC AAC TGG TAC GTG GAC GGC GTG GAG         1212
Glu Asp Pro Glu Val Lys Phe Asn Trp Tyr Val Asp Gly Val Glu
         40                  45                  50

GTG CAT AAT GCC AAG ACA AAG CCG CGG GAG GAG CAG TAC AAC AGC         1257
Val His Asn Ala Lys Thr Lys Pro Arg Glu Glu Gln Tyr Asn Ser
         55                  60                  65

ACG TAC CGG GTG GTC AGC GTC CTC ACC GTC CTG CAC CAG GAC TGG         1302
Thr Tyr Arg Val Val Ser Val Leu Thr Val Leu His Gln Asp Trp
         70                  75                  80

CTG AAT GGC AAG GAG TAC AAG TGC AAG GTC TCC AAC AAA GCC CTC         1347
Leu Asn Gly Lys Glu Tyr Lys Cys Lys Val Ser Asn Lys Ala Leu
         85                  90                  95

CCA GCC CCC ATC GAG AAA ACC ATC TCC AAA GCC AAA GGTGGGACCC         1393
Pro Ala Pro Ile Glu Lys Thr Ile Ser Lys Ala Lys
        100                 105                 110

GTGGGGTGCG AGGGCCACAT GGACAGAGGC CGGCTCGGCC CACCCTCTGC CCTGAGAGTG   1453

ACCGCTGTAC CAACCTCTGT CCTACA GGG CAG CCC CGA GAA CCA CAG GTG TAC   1506
                             Gly Gln Pro Arg Glu Pro Gln Val Tyr
                              1                   5

ACC CTG CCC CCA TCC CGG GAT GAG CTG ACC AAG AAC CAG GTC AGC         1551
Thr Leu Pro Pro Ser Arg Asp Glu Leu Thr Lys Asn Gln Val Ser
         10                  15                  20

CTG ACC TGC CTG GTC AAA GGC TTC TAT CCC AGC GAC ATC GCC GTG         1596
Leu Thr Cys Leu Val Lys Gly Phe Tyr Pro Ser Asp Ile Ala Val
         25                  30                  35

GAG TGG GAG AGC AAT GGG CAG CCG GAG AAC AAC TAC AAG ACC ACG         1641
Glu Trp Glu Ser Asn Gly Gln Pro Glu Asn Asn Tyr Lys Thr Thr
         40                  45                  50

CCT CCC GTG CTG GAC TCC GAC GGC TCC TTC TTC CTC TAC AGC AAG         1686
Pro Pro Val Leu Asp Ser Asp Gly Ser Phe Phe Leu Tyr Ser Lys
         55                  60                  65

CTC ACC GTG GAC AAG AGC AGG TGG CAG CAG GGG AAC GTC TTC TCA         1731
Leu Thr Val Asp Lys Ser Arg Trp Gln Gln Gly Asn Val Phe Ser
         70                  75                  80

TGC TCC GTG ATG CAT GAG GCT CTG CAC AAC CAC TAC ACG CAG AAG         1776
Cys Ser Val Met His Glu Ala Leu His Asn His Tyr Thr Gln Lys
         85                  90                  95

AGC CTC TCC CTG TCT CCG GGT AAA TGAGTGCGAC GGCCGGCAAG CCCCGCTCCC    1830
Ser Leu Ser Leu Ser Pro Gly Lys
100                 105

CGGGCTCTCG CGGTCGCACG AGGATGCTTG GCACGTACCC CCTGTACATA CTTCCCGGGC   1890

GCCCAGCATG GAAATAAAGC ACCCAGCGCT GCCCTGGGCC CCTGCGAGAC TGTGATGGTT   1950

CTTTCCACGG GTCAGGCCGA GTCTGAGGCC TGAGTGGCAT GAGGGAGGCA GAGCGGGTC    2009
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:

(B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:6:

Gly Arg Gly Asp
 1

(2) INFORMATION FOR SEQ ID NO:7:

(i) SEQUENCE CHARACTERISTICS:
                (A) LENGTH: 44 base pairs
                (B) TYPE: nucleic acid
                (C) STRANDEDNESS: single
                (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:7:

GAAGAGCCTC TCCCTCGGCC GGGGCGACTC TCCGGGTAAA TGAG      44

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:8:

G AAG AGC CTC TCC CTG TCT CCG GGT AAA TGAG  32
  Lys Ser Leu Ser Leu Ser Pro Gly Lys
   1                5

( 2 ) INFORMATION FOR SEQ ID NO:9:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:9:

G AAG AGC CTC TCC CTC GGC CGG GGC GAC TCT CCG GGT AAA TGAG  44
  Lys Ser Leu Ser Leu Gly Arg Gly Asp Ser Pro Gly Lys
   1                5                    10

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:10:

Thr Gly Arg Gly Asp Ser Pro
 1               5

(2) INFORMATION FOR SEQ ID NO:11:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:

(A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:11:

ACCGTGGACA AGAGCACCGG CCGGGGCGAC AGCCCTAGGT GGCAGCAGGG G          51

(2) INFORMATION FOR SEQ ID NO:12:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: Genomic DNA (iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:

( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:12:

```
ACC  GTG  GAC  AAG  AGC  AGG  TGG  CAG  CAG  GGG                              30
Thr  Val  Asp  Lys  Ser  Arg  Trp  Gln  Gln  Gly
 1              5                        10
```

( 2 ) INFORMATION FOR SEQ ID NO:13:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: Genomic DNA ( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:13:

```
ACC  GTG  GAC  AAG  AGC  ACC  GGC  CGG  GGC  GAC  AGC  CCT  AGG  TGG  CAG     45
Thr  Val  Asp  Lys  Ser  Thr  Gly  Arg  Gly  Asp  Ser  Pro  Arg  Trp  Gln
 1              5                        10                       15

CAG  GGG                                                                      51
Gln  Gly
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL: NO ( i v ) ANTI-SENSE: NO ( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION: 1-20
        ( C ) IDENTIFICATION METHOD:
        ( D ) OTHER INFORMATION: /note="E primer"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:14:

GGGCTCTCGC GGTCGCACGA 20

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL: NO ( i v ) ANTI-SENSE: YES ( v ) FRAGMENT TYPE:

( v i ) ORIGINAL SOURCE:
        ( A ) ORGANISM:

-continued

```
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION: 1-29
            ( C ) IDENTIFICATION METHOD:
            ( D ) OTHER INFORMATION: /note="E primer"

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:15:

CCCGGATCCG   TGGAAAGAAC   CATCACAGT                                                  29
```

ARTIFICIAL ANTIBODY

This application is a continuation of now abandoned application, Ser. No. 07/752,668, filed Jul. 3, 1991.

This invention relates to an artificial antibody, and in particular, to a multifunctional artificial antibody to which a new function of artificial cell-adhesive activity has been introduced.

With the recent advances in molecular biology, the mechanisms by which cells and the extracellular matrix adhere are coming to be understood on the molecular level. Of the extracellular matrix proteins, Fibronectin (FN) was the first found to contain an essential sequence for cell adhesion. Thus the Arg-Gly-Asp-Ser sequence (hereinafter referred to as R-S sequence: SEQ ID No. 1) in the cell-binding domain of FN has been found to be essential for cell adhesion by Ruoslahti et al. (Nature, 309, 30–33, 1984). The RGD part of this sequence is needed for cell adhesion and substitution for other amino acids cannot done without loss of cell-adhesive activity, but the serine can be replaced by, for example, threonine, alanine, cysteine, or valine without loss of activity. However, if substitution is with proline or lysine, the activity is lost. Proteins other than FN that contain the sequence RGD include thrombin, vitronectin, yon Willebrand factor, fibrinogen, collagen, discoidin I, λ-phage receptor, and others. It has thus been suggested that the RGD sequence is closely related to protein functions (Ruoslahti et al. Proc. Natl. Acad. Sci. USA, 81, 5985–5988, 1984). However, it is not certain whether the RGD sequence in these molecules confers cell-adhesive activity. For example, although fibrinogen has the R-S sequence, it does not have cell-adhesive effects on fibroblasts.

Another example of a cell-adhesive protein in addition to those named above is laminin. Laminin is a glycoprotein of high molecular weight found in the basement membrane, and it has cell-adhesive activity toward a variety of cells in the epithelium. It has been reported (Graf et al., Cell, 48,989–996, 1987) that the smallest sequence related to cell adhesion is Tyr-Ile-Gly-Ser-Arg (hereinafter referred to as Y-R sequence: SEQ ID No. 2). Laminin also has the RGD sequence, but it is not known if the sequence is related to the cell-adhesive activity.

In addition, it is known that the Glu-Ile-Leu-Asp-Val (hereinafter referred to as E-V sequence: SEQ ID No. 3) sequence in the IIICS domain of FN is related to the adhesion of lymph cells and melanoma cells.

Antibodies are produced in vivo following a stimulus by an antigen, and they bind specifically to the antigen that provided this stimulation. Immunoglobulins (Igs) have this function, and they have been classified into subclasses IgG, IgA, IgM, IgD, and IgE, each of which has a basic structure made up of a combination of heavy (H) chains and light (L) chains. Antibodies contain a constant region and a variable region. The constant region has a constant sequence of amino acids that is decided genetically. The variable region is the binding site of the antibody to its antigen; the sequence of amino acids depends on the antigen for which the antibody is specific.

Antibodies have multiple functions. Some antibodies act as agglutinins, precipitins, hemolysins, or antitoxins, and some lave complement-fixing, virus-neutralizing, or anaphylatic activities. So far, an antibody that has the function of cell-adhesive activity like that of FN and laminin mentioned above has not been found.

In the self-defense mechanism of the body, there are R-S sequence-dependent receptors on the surfaces of the macrophages, which carry out phagocytosis (FEBS Letters 242, 378–382, 1989). By the insertion of a peptide with cell-adhesive activity such as the R-S sequence into the appropriate region of an antibody molecule, it is possible to accelerate the phagocytosis of immune complexes, which consist of a foreign substance and an antibody. Probably other activities of cells involved in cell immunity can also be increased. By an increase in the affinity of said antibodies to various kinds of cells with different functions in the body, it is possible to enhance the functioning of the antibodies in the different cells and tissues.

Thus the object of this invention is to provide an antibody with antigen-binding activity, in which has been introduced affinity for cells, and macrophages in particular, and also to provide a method for the production of such antibodies.

Briefly, this invention relates to a novel artificial antibody having an antigen binding activity and an artifical cell-adhesive activity. This invention also relates to a DNA which codes for a constant region of H-chain of an artificial antibody, said constant region having been introduced with an amino acid sequence having an artificial cell-adhesive activity.

In the present invention it is possible to use as the antibody any substance that has the immunological specificity to antigen and has antigen-binding activity. Thus, a fragment such as the Fab fragment, for example, can be used. By artificial cell-adhesive activity is meant the following. An amino acid sequence with cell-adhesive activity can be inserted into the antibody molecule in question or substituted for the usual amino acid sequence of the antibody in question by the use of the methods of protein engineering and genetic engineering. Artificial cell-adhesive activity is the newly expressed activity that results by such insertion or substitution. Sequences of amino acids that have cell-adhesive activity include, for examples, the RGD, Y-R, and E-V sequences mentioned above. Any sequence that can confer cell-adhesive activity on antibodies can be used. Said amino acid sequence can be introduced at any position in the antibody molecule that is exposed on the surface of the three-dimensional structure of the antibody molecule. To obtain the most suitable artificial antibody, the amino acid sequence with cell-adhesive activity can be selected by identification of a suitable position of said sequence and by measurement of the cell-adhesive activity.

The DNA sequence that codes for the amino acid sequence with cell-adhesive activity described above can be inserted into a sequence of DNA that codes for any antibody that can be expressed by the use of genetic engineering, so that said DNA sequence that codes for the amino acid sequence with cell-adhesive activity is connected in the correct position for it to function as an open reading frame. Then plasmids that carry this DNA sequence are used to transform cells that are capable of producing the antibody. These transformants are cultured by tissue culture or else allowed to replicate in a living organism, so that the artificial antibody that is to be produced is obtained.

Antibodies that have been expressed by the use of genetic engineering include, for example, anti-phosphorylcholine IgG ( FEBS Letters, 244, 303–306, 1989) . Said antibody is a human/mouse chimera antibody. Plasmid pSV2HG1Vpc that carries the DNA sequence that codes for the H-chain variable region of the mouse anti-phosphorylcholine antibody and the DNA that codes for the H-chain constant region of human IgG gamma-type and also plasmid pSV2HC$_\kappa$Vpc that carries the DNA sequence that codes for the L-chain variable region of murine anti-phosphorylcholine antibody and the L-chain constant region of human IgG Kappa-type are used to transform murine melonoma SP 2/0 cells for the production of this antibody. The DNA sequence that codes for this antibody, which can be, for example, the DNA sequence that codes for the CH3 region of the H-chain constant region of human IgG gamma-type, has inserted in its sequence by site-directed mutagenesis a DNA sequence, such as, for example, the DNA sequence that codes for the R-S sequence described above, and is connected in this way with the DNA sequence that codes for this amino acid sequence with cell-adhesive activity as an open reading frame. This modified DNA sequence that codes for the H-chain constant region of human IgG gamma-type and the DNA sequence that codes for the H-chain variable region of mouse anti-phosphorylcholine antibody are connected, and plasmids that carry this DNA fragment, such as, for example, plasmid pSV2HC$_x$Vpc, are used to transform SP 2/0 cells, by which means it is possible to obtain cells that produce anti-phosphorylcholine antibody to which a cell-adhesive amino acid sequence has been introduced.

The antibody produced by recombinants can be purified if necessary by the use of ion-exchange chromatography, affinity chromatography, and the like.

By use of the procedures of protein engineering and genetic engineering, it is possible to produce cell-adhesive activity of the antibody into which an amino acid sequence with cell-adhesive activity has been introduced, and it is possible to measure the introduced cell-adhesive activity by, for example, the method of Ruoslahti (Methods in Enzymology, 82, 803–831, 1981). The sample to be tested is dissolved in phosphate-buffered saline (PBS) or the like and allowed to adsorb to the wells of a microtitre plate. Then blocking is done with bovine serum albumin (BSA), and either baby hamster kidney (BHK) cells or normal rat kidney (NRK) cells are placed in the wells and incubated at 37° C. The cells are examined under a microscope for spreading, by which means the cell-adhesive activity of the sample to be tested is evaluated. When this was done, anti-phosphorylcholine antibody that did not contain the R-S sequence was found not to have cell-adhesive activity, but anti-phosphorylcholine antibody that did contain the introduced R-S sequence had cell-adhesive activity in addition to its antigen-binding activity: A substance such as phosphorylcholine KLH, for example, can be used to measure the antigen-binding activity of said modified or non modified antibody. In this way, it was found that cell-adhesive activity depended on the presence of the RGDS sequence. When the S of the sequence RGDS was replaced by other amino acids, such as, for example, V, A, T, C, or F, cell-adhesive activity was found, so the S of the sequence RGDS may be replaced by V, A, T, C, F, or so on. Also, insertion of the cell-adhesive sequence, R-S, Y-R, or E-V sequence may be in an appropriate restriction site with gene engineering techniques. When there is no appropriate restriction site, site-directed mutagenesis can be used to insert the desired amino acid sequence in the appropriate position. However, it is difficult to predict if cell-adhesive activity will be conferred. It is an important point whether the inserted site has a three-dimensional structure which can be recognized by cell receptors.

The DNA that codes for the constant region of H-chain and the introduced amino acid sequence that has cell-adhesive activity can be connected with the DNA that codes for the variable region of the H-chain, and by this means, the DNA that codes for the H-chain of the antibody that has an amino acid sequence with cell-adhesive activity can be obtained.

As the DNA that codes for the constant region of H-chain that has an introduced amino acid sequence that has cell-adhesive activity, there is, for example, a DNA sequence of SEQ ID No. 4 that codes for the constant region of an H-chain of human IgG gamma-type into which the R-S sequence has been inserted. Plasmid pSV2·HG1·gpt·CT2 carries the DNA sequence of SEQ ID No. 4 and by the use of *Escherichia coli* HB101/CT2(FERM BP-3399) that has been transformed with said plasmid, the plasmid pSV2·HG1·gpt·CT2 can be prepared easily. In this plasmid, any DNA that codes for the variable region of H-chain can be inserted readily, and combined with any plasmid that can produce the desired L-chain, so that by use of genetic engineering, it is possible to produce readily an artificial antibody to which cell-adhesive activity has artificially been introduced. As the variable region of the H-chain, either the human type or mouse type can be used, and as the antigen to be recognized, there are, for example, tumor antigens and sugar-chain antigens.

As explained in detail above, by this invention, it is possible to provide an antibody that has strengthened affinity for cells by the artificial introduction of cell-adhesive activity.

These multifunctional antibodies are of use in the self-defense mechanism of organisms that involves antibodies and effector cells. In addition, the movement of the antibodies to the tissues is increased, so the effects of the antibodies are increased in the tissues, as well.

The invention will be explained in more detail by means of the following Examples which refer partly to the accompanying drawings wherein.

EXAMPLE 1

Construction of R-S sequence containing IgG expression vector (1) Construction of pUCCT1 and pUCCT2

A plasmid pSV2-HG1gpt that was previously constructed by these inventors (FEBS Letters, 244, 303–306, 1989) contains a structural gene coding for the constant region of the human IgG heavy chain. The structure of pSV2-HG1gpt is shown in FIG. 1 and the partial DNA sequence of the structural gene is represented by the sequence of SEQ ID No.5 in the Sequence Listing.

Figure 2:
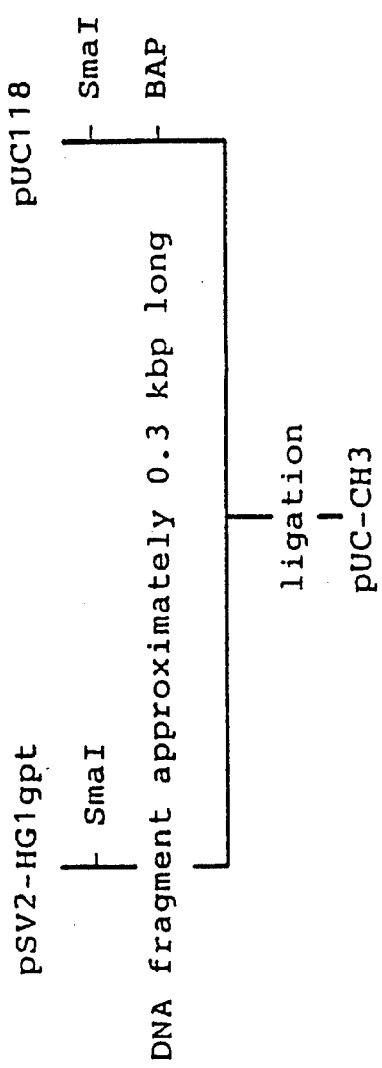
FIG. 2 shows the partial restriction map and the structure of the region coding for the constant region of the human IgG heavy chain shown in FIG. 1.
Figure 1:
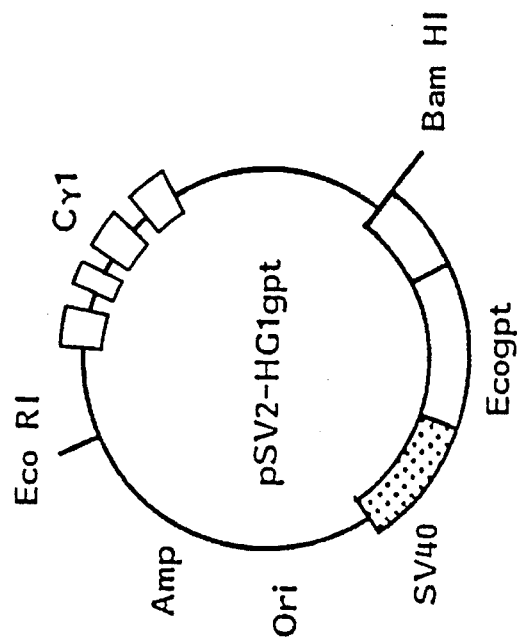
FIG. 1 shows the structure of pSV2-HG1gpt.

FIG. 1 is a figure showing the structure of pSV2-HG1gpt and FIG. 2 is a figure showing the partial restriction map and the structure of the region coding for the constant region of the human IgG heavy chain shown in FIG. 1. In the sequence of SEQ ID No.5. base No. 209-502 is a region coding for CH1 and base No. 891-935 is a region coding for the hinge region and base No. 1054-1383 is a region coding for CH2 and base No. 1480-1800 is a region coding for CH3. Base No. 1832-1851 1939-1060 are sequences for preparation of primers for PCR, and base No. 1902 -1908 is the poly(A) addition signal sequence.

First, 115 µg of plasmid pSV2-HG1gpt was digested with 50 units of SmaI in 105 µl of a reaction mixture containing buffer T for use in restriction enzyme reactions (33 mM Trisacetate. pH 7.9. 10 mM magnesium acetate, 0.5 mM dithiothreitol, and 66 mM potassium acetate) at 37° C. for 2 hours. Then the digest was treated by 6% polyacrylamide gel electrophoresis, and fragments approximately 0.3 kbp long that contained the region coding for almost all of the CH3 domain of the IgG heavy chain were obtained.

Next, 5 µg of pUC118 was digested with 10 units of SmaI in 26 µl of a reaction mixture containing buffer T for use in restriction enzyme reactions at 37° C. for 2 hours. Then 0.6 unit of bacterial alkaline phosphatase from *Escherichia coil* was added and the mixture was incubated at 65° C. for 1 hour. An equal volume of phenol saturated with TE buffer (10 mM Tris-HCl, pH 8.0, and 1 mM EDTA) was added and mixed by being vortexed. The mixture was centrifuged at 12000 rpm for 5 minutes at 25° C. and the two phases obtained were separated. An equal volume of a 1:1 mixture (v/v) of the phenol saturated with TE buffer and chloroform was added to the aqueous phase and mixed by being vortexed. The mixture was centrifuged at 12000 rpm for 5 minutes and the two phases obtained were separated. An equal volume of chloroform was added to the aqueous phase and mixed by being vortexed. The mixture was centrifuged at 12000 rpm for 5 minutes and the upper phase was obtained. The DNA fragment was recovered from this aqueous phase by ethanol precipitation.

Figure 3:
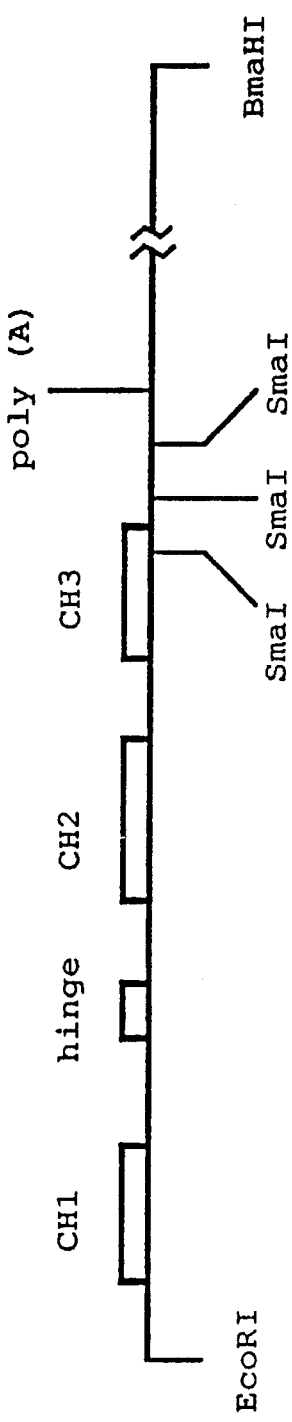
FIG. 3 shows the process of construction of the plasmid pUC-CH3.

This dephosphorylated digest of pUC118 by SmaI and the fragment approximately 0.3 kbp long that contained the region coding for almost all of the CH3 domain of the IgG heavy chain obtained as described above were mixed and incubated in 11.5 µl of a reaction mixture containing ligation buffer (66 mM Tris-HCl, pH 7.6, 6.6 mM MgCl$_2$, 10 mM dithiothreitol, 0.5 mM ATP, and 10% PEG 6000) at 37° C. for 1 hour. A portion of the reaction mixture was used to transform *E. coli* DH5 cells. These transformed cells were spread over the surface of plates of LB agar (1% tryptone, 0.5% yeast extract, 0.5% NaCl, and 1.5% agar) containing 50 µg/ml ampicillin and incubated overnight at 37° C. Single colonies of cells grown on the plate were inoculated into 2 ml of LB broth (1% tryptone, 0.5% yeast extract, and 0.5% NaCl) containing 50 µg/ml ampicillin and cultivated overnight at 37° C. with shaking at 230 rpm. From these cultured cells, plasmids were extracted. Samples of the plasmids obtained were digested with 10 units of SmaI and 0.5 µg of RNase A in 10 µl of a reaction mixture containing buffer T for use in restriction enzyme reactions at 37° C. for 2 hours. Tile reaction mixture was then treated by 6% polyacrylamide gel electrophoresis, and plasmids carrying the DNA fragments approximately 0.3 kbp long were selected. Samples of these plasmids were digested with 12 units of BamHI, 10 units of NsiI, and 0.5 µl of RNase A in 20 µl of a reaction mixture containing buffer H for use in restriction enzyme reaction (50 mM Tris-HCl, pH 7.5, 10 mM MgCl$_2$, 1 mM dithiothreitol, and 100 mM NaCl) at 37° C. for 2 hours. The reaction mixtures were treated by 6% polyacrylamide gel electrophoresis, and a plasmid carrying the DNA fragment approximately 230 bp long was selected. The plasmid was named pUC-CH3. The construction of pUC-CH3 is summarized in FIG. 3.

For site-directed mutagenesis, single-stranded DNA, dU-ssDNA pUC-CH3, was prepared from this pUC-CH3 by the method of Kunkel as follows.

First, pUC-CH3 was used to transform of *E. coli* MV1184 cells. These transformed cells were spread over the surface plates of LB agar containing 150 µg/ml ampicillin and incubated overnight at 37° C. Single colonies of cells grown on the plates were inoculated into 2 ml of LB broth containing 150 µg/ml ampicillin and cultivated overnight at 37° C. with shaking at 230 rpm. Then 10 µl of the overnight culture and 20 µl of helper phage M13KO7 were added into 2 ml of 2YT broth (1.6% Bactotrypton, 1% yeast extract, and 0.5% NaCl) containing 150 µg/ml ampicillin and the mixture was incubated at 37° C. for 30 minutes. Kanamycin was added to the culture to the final concentration of 70 µg/ml, and the cells were cultivated at 37° C. for 16 hr with shaking at 230 rpm. The culture was centrifuged at 12000 rpm and 4° C. for 10 minutes and the culture supernatant was obtained. Next, 20 µl of the supernatant was added to a culture of *E. coli* BW313 cells to transform them. The transformed cells were spread on the surface of plates of LB agar plates containing 150 µg/ml ampicillin and incubated overnight at 37° C. A single colony of cells grown on the plates and 20 µl of helper phage M13KO7 was used to inoculate 2 ml of 2YT broth containing 150 µg/ml ampicillin and incubated at 37° C. for 30 minutes. Kanamycin was added to the culture to the final concentration of 70 µl/ml. The cells were cultivated at 37° C. overnight with shaking at 230 rpm. Then 1.5 ml of this culture was centrifuged at 12000 rpm for 10 minutes at 4° C., and 1 ml of the supernatant was sampled. Next, 250 µl of 20% PEG 6000-2.5 M NaCl was added to the supernatant and the mixture was incubated at room temperature for 30 minutes before being centrifuged at 12000 rpm for 10 minutes. The precipitate was dissolved in 100 µl of TE buffer. Single-stranded DNA incorporating deoxyuridine (dU), named dU-ssDNA pUC-CH3 below, was obtained by phenol extraction and ethanol precipitation.

C1788-A1789 in the DNA sequence coding for the CH3 region was selected as the position for a sequence coding for cell-adhesive activity to be added. DNA coding for the R-S sequence was introduced when the DNA sequence coding for amino acid sequence of SEQ ID No.6 was inserted at that position.

The DNA fragment for use in mutagenesis, with sequence of SEQ ID No.7 in the table of sequences, was synthesized with a DNA synthesizer and deblocked. This fragment was purified by polyacrylamide gel electrophoresis and phosphorylated with use of T4 polynucleotide kinase. Next, 0.2 pmol of dU-ssDNA pUC-CH3 and 1 pmol of this phosphorylated fragment were treated in 10 µl of a reaction mixture containing 20 mM Tris-HCl, pH 8.0, 10 mM MgCl$_2$, 5 mM NaCl, and 1 mM dithiothreitol at 65° C. for 15 minutes, and annealed by being left at 37° C. for 15 minutes. Then, 25 µl of the solution containing 50 mM Tris-HCl, pH 8.0, 0.60 mM ammonium acetate, 5 mM MgCl$_2$, 5 mM dithiothreitol, 1 mM NAD, and 0.5 mM dNTP (G, A, T, and C) was added to this reaction mixture after it was left for 15 minutes, and 1 unit of T4 DNA polymerase and 60 units of T4 DNA ligase were added to this mixture. This mixture was incubated at 25° C. for 120 minutes, so that double-stranded DNA was synthesized. A portion of the double-stranded DNA was used to transform *E. coli* BMH 71-18 mutS cells. These transformed cells were transfected with helper phage M13KO7 and then cultivated at 37° C. overnight with shaking at 230 rpm. This overnight culture was centrifuged at 12000 rpm and 4° C. for 5 minutes and the supernatant was obtained. A portion of this supernatant was added to an overnight culture of E. coli MV1184 cells and spread on the surface of plates of LB agar containing 150 µl/ml ampicillin. The plates were incubated overnight at 37° C. Single colonies of cells grown on the plates were used to inoculate 2YT broth containing 150 µg/ml ampicillin. Then 20 µl of the helper phage M13KO7 was added to the culture and the mixture was incubated at 37° C. for 30 minutes. Kanamycin was added to the culture to the final concentration of 70 µg/ml. The culture was cultivated overnight at 37° C. with shaking at 230 rpm. The overnight culture was centrifuged at 12000 rpm and 4° C. for 10 minutes, and 1 ml of the supernatant was sampled. To this, 250 µl of 20% PEG 6000 in 2.5 M NaCl was added to the supernatant, which was left at room temperature for 30 minutes and then centrifuged at 12000 rpm and 4° C. for 10 minutes. The precipitate obtained was dissolved in 100 µl of TE buffer, and single-stranded DNA was purified from this phage solution by phenol extraction and ethanol precipitation. The single-stranded DNAs obtained were analyzed by the dideoxy sequencing method. DNA the sequence of which was changed at one region from that of sequence of SEQ ID No.8 to that of sequence of SEQ ID No.9 was selected, and double-stranded DNA was prepared. The DNA was named pUCCT1.

C1704-A1705 in the DNA sequence coding for the CH3 region, which has the sequence of SEQ ID No.5, was selected as the position for a sequence coding for the cell-adhesive activity to be added. DNA coding for the R-S sequence was introduced at this position by the insertion of the DNA sequence coding for the amino acid sequence of SEQ ID No.10. The DNA fragment for use in mutagenesis with the sequence of SEQ ID No.11 was synthesized with a DNA synthesizer, deblocked, and purified by polyacrylamide gel electrophoresis. With use of the DNA fragment for mutagenesis and the dU-ssDNA pUC-CH3 described above, a plasmid carrying a DNA changed at one region to the sequence of SEQ ID No.13 was selected and double-stranded DNA was obtained. The DNA was named pUCCT2.

(2) Preparation of poly(A) fragments

The poly (A) addition signal sequence related to transcription is located downstream of the gene coding for the CH3 domain of the human IgG heavy chain. For preparation of fragments containing a downstream portion of the fragment approximately 0.3 kbp long described above and this poly(A) signal, two DNA sequences, SEQ ID No.14 and 15 were synthesized and phosphorylated by the methods described above. The polymerase chain reaction (PCR; Saiki et al., Science, 230:1350– 1353, 1985) was performed with these synthetic oligonucleotides as the primers and with pSV2-HG1gpt as the template. A DNA fragment approximately 130 bp long was amplified in this way with use of 2.5 units of Taq DNA polymerase in 100 µl of a reaction buffer containing 50 mM KCl, 10 mM Tris-HCl, pH 8.3, 1.5 mM $MgCl_2$, and 0.01% gelatin. During PCR, the reaction mixture was incubated at three temperatures in each cycle: at 94° C. for 2 minutes for amplification and denaturation, at 37° C. for 3 minutes for annealing, and at 72° C. for 4 minutes for extension. After 25 cycles of PCR, the amplified DNA fragment was purified by phenol extraction and ethanol precipitation and dissolved in 50 µl of TE buffer. The amplified DNA was named POLAPCR.

Figure 4:
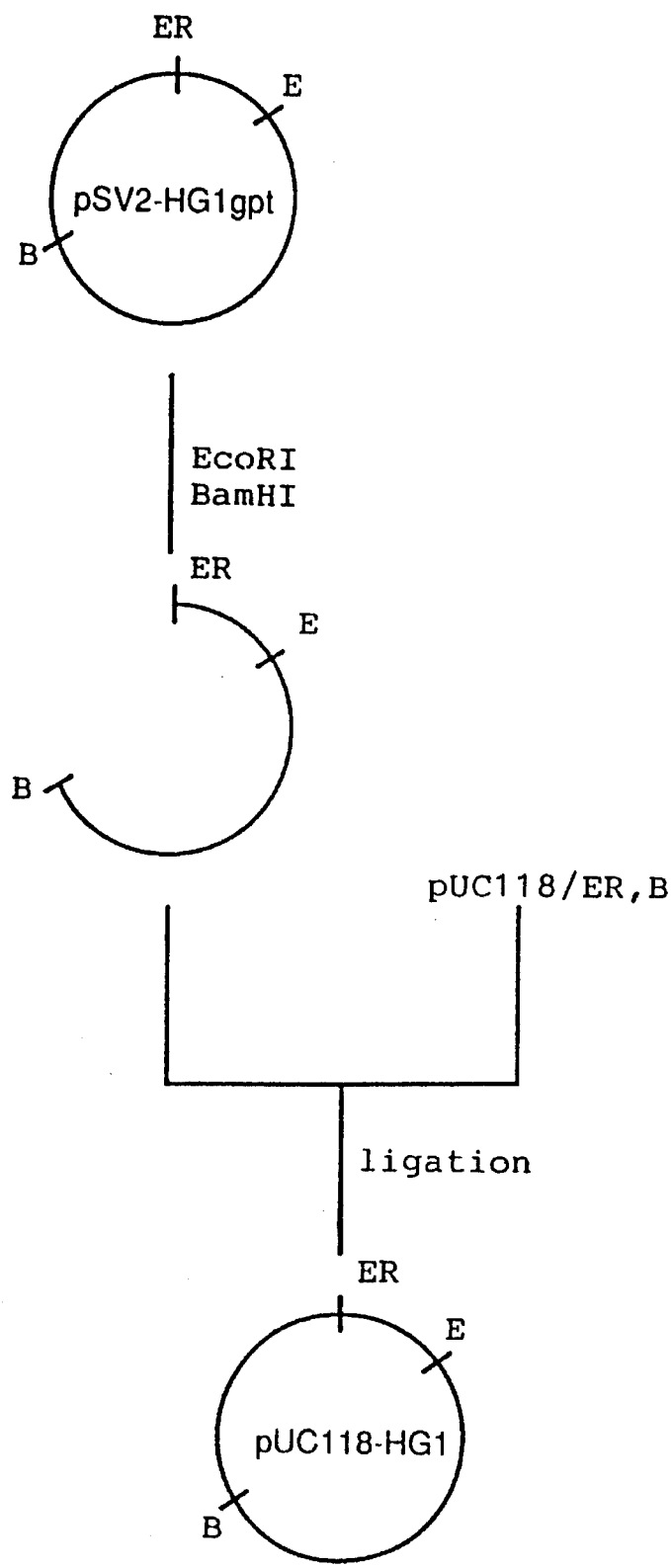
FIG. 4 shows the process of construction of the plasmid pUC118-HG1 and restriction map.

(3) Subcloning of DNA fragment containing the genes coding for the constant region of the IgG heavy chain First, 57.5 µg of pSV2HG1gpt was digested with 30 units of EcoRI and 30 units of BamHI in 105 µl of a reaction mixture containing buffer H for use in restriction enzyme reactions at 37 ° C. for 2 hours. After digestion, the reaction mixture was treated by 0.5% agarose gel electrophoresis. A DNA fragment approximately 8.5 kbp long was obtained by electroelution. The DNA fragment eluted was purified by phenol extraction and ethanol precipitation and dissolved in 50 µl of TE buffer. A portion of the purified DNA fragment and 0.2 µg of pUC118 digested by EcoRI and BamHI and dephosphorylated with E. coli alkaline phosphatase were incubated with 300 units of T4 DNA ligase in 20 µl of a reaction mixture containing ligation buffer at 37° C. for 1 hour. After the reaction, a portion of this reaction mixture was used to transform E. coli DH5 cells. The transformed cells were spread over the surface of plates of LB agar containing 50 µl/ml ampicillin and incubated overnight at 37° C. Single colonies of cells grown on the plates were inoculated into 2 ml of LB broth containing 50 µg/ml ampicillin and cultivated overnight at 37° C. with shaking at 230 rpm. From these cultured cells, plasmids were extracted. Samples of the plasmids were digested with 12 units of EcoRI, 12 units of BamHI, and 0.5 µg of RNase A in 10 µl of a reaction mixture containing buffer H for use in restriction enzyme reactions at 37 ° C. for 2 hours. The reaction mixture was treated by 1% agarose gel electrophoresis. The plasmid carrying the DNA fragment approximately 8.5 kbp long was selected and named pUC118-HG1. The structure and restriction map of this plasmid are shown in FIG. 4. In this and other figures, ER indicates EcoRI, E indicates EcoT22I, and B indicates BamHI.

Figure 5:
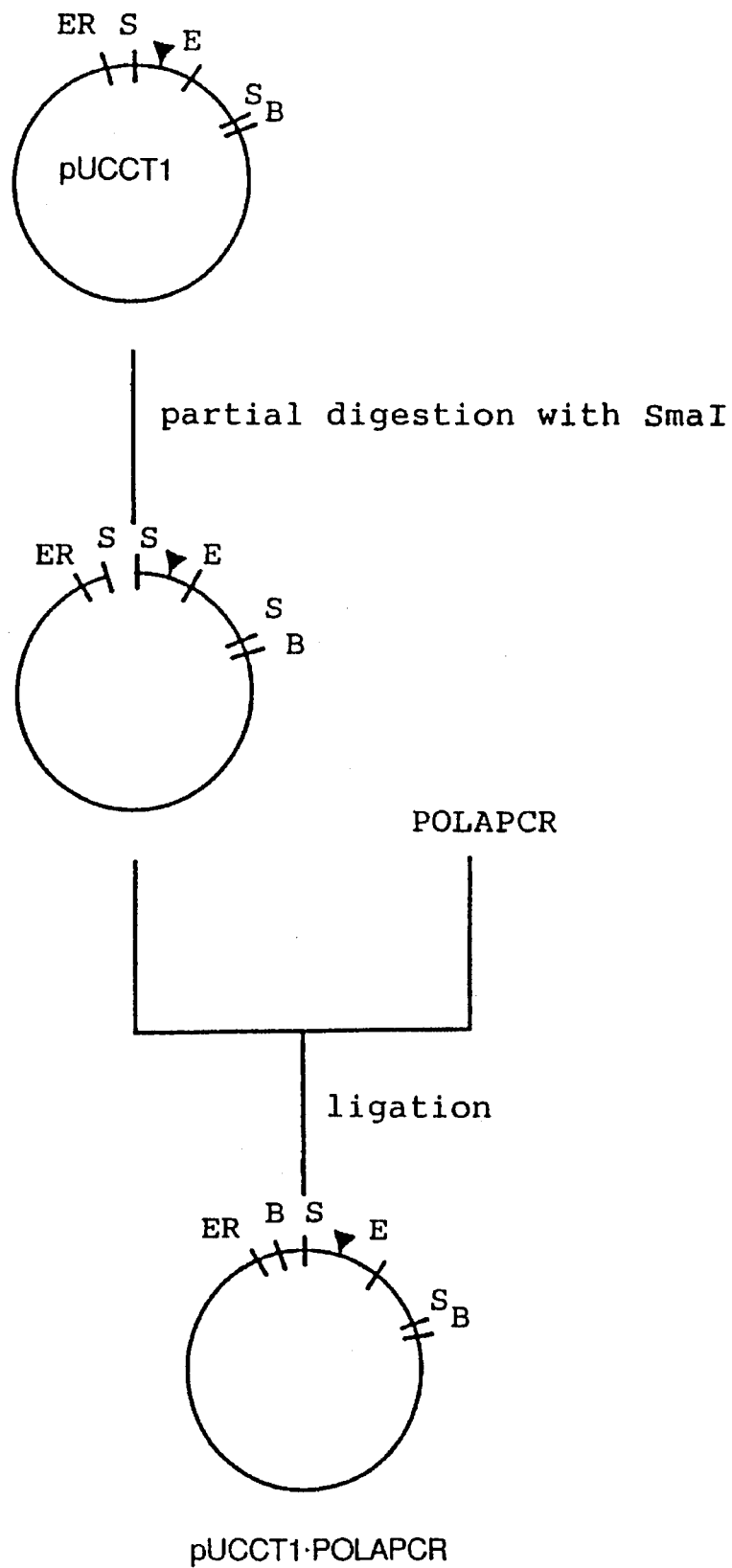
FIG. 5 shows the process of construction of the plasmid pUCCT1·POLAPCR and restriction map.

(4) Construction of mutagenized pSV2-HG1gpt (i) First, 17.4 µg of pUCCT1 was partially digested with 7.5 units of SmaI in 60.75 µl of a reaction mixture containing buffer T for use in restriction enzyme reaction. The reaction was started by addition of the enzyme, and 10-µl portions were sampled at 30, 60, 90, 210, and 270 seconds. The reaction was stopped by the mixture of each portion with phenol saturated with TE buffer. The DNA was obtained by ethanol precipitation and dissolved in 50 µl of TE buffer. The DNA fragments were dephosphorylated with 1.2 units of E. coli alkaline phosphatase at 65° C. for 1 hour, obtained by phenol extraction and ethanol precipitation, and dissolved in 50 µl of TE buffer. Then 10 µl of the DNA solution and 10 µl of POLAPCR were mixed with and allowed to react with 300 units of T4 DNA ligase in a reaction mixture containing ligation buffer at 37° C. for 1 hour. The digest of pUCCT1 partially digested with SmaI was ligated with POLAPCR. A portion of the reaction mixture was used to transform E. coli MV1184 cells. The transformed cells were spread over the surface of plates of LB agar containing 50 µl/ml ampicillin and incubated overnight at 37° C. Single colonies of cells grown on the plates were inoculated into 2 ml of LB broth containing 50 µg/ml ampicillin and were cultivated overnight at 37° C. with shaking at 230 rpm. Plasmids were extracted from these cultured cells and dissolved in 50 µl of TE buffer. A portion of the plasmids obtained was digested with 10 units of BamHI and 0.5 µg of RNase A in 15 µl of a reaction mixture containing buffer H for restriction enzyme reactions at 37° C. for 2 hours. The reaction mixtures were treated by 2% agarose gel electrophoresis, and the plasmid carrying a DNA fragment approximately 450 bp long was selected and named pUCCT1·POLAPCR. The structure and restriction map of the plasmid are shown in FIG. 5. In this and other figures, ▼ indicates a site at which DNA coding for the amino acid sequence of SEQ ID NO.6 is inserted, and S indicates SmaI. Next, 20 µl of the plasmid pUCCT1·POLAPCR was allowed to react with 12 units of EcoT22I, 12 units of BamHI, and 0.25 µg of RNase A in 30 µl of a reaction mixture containing buffer H for restriction enzyme reactions at 37° C. for 2 hours. The reaction mixture was treated by 2% agarose gel electrophoresis. The DNA fragment approximately 220 bp long was obtained from the gel with use of DEAE-cellulose paper and a DNA solution was obtained from the paper. The DNA fragment was purified from the DNA solution by phenol extraction and ethanol precipitation, and dissolved in 50 µl of TE buffer for use in ligation reactions as follows. First, 25 µl of pUC118-HG1 was digested with 12 units of EcoRI, 12 units of EcoT22I, and 0.25 µg of RNase A in 30 µl of a reaction mixture containing buffer H for restriction enzyme reactions at 37° C. for 2 hours. The reaction mixture was treated by 1% agarose gel electrophoresis. The DNA fragment approximately 1750 bp long was obtained from the gel with use of DEAE-cellulose paper, and a DNA solution was obtained from the paper. The DNA fragment was purified from the DNA solution by phenol extraction and ethanol precipitation, and dissolved in 50 µl of TE buffer.

Figure 6:
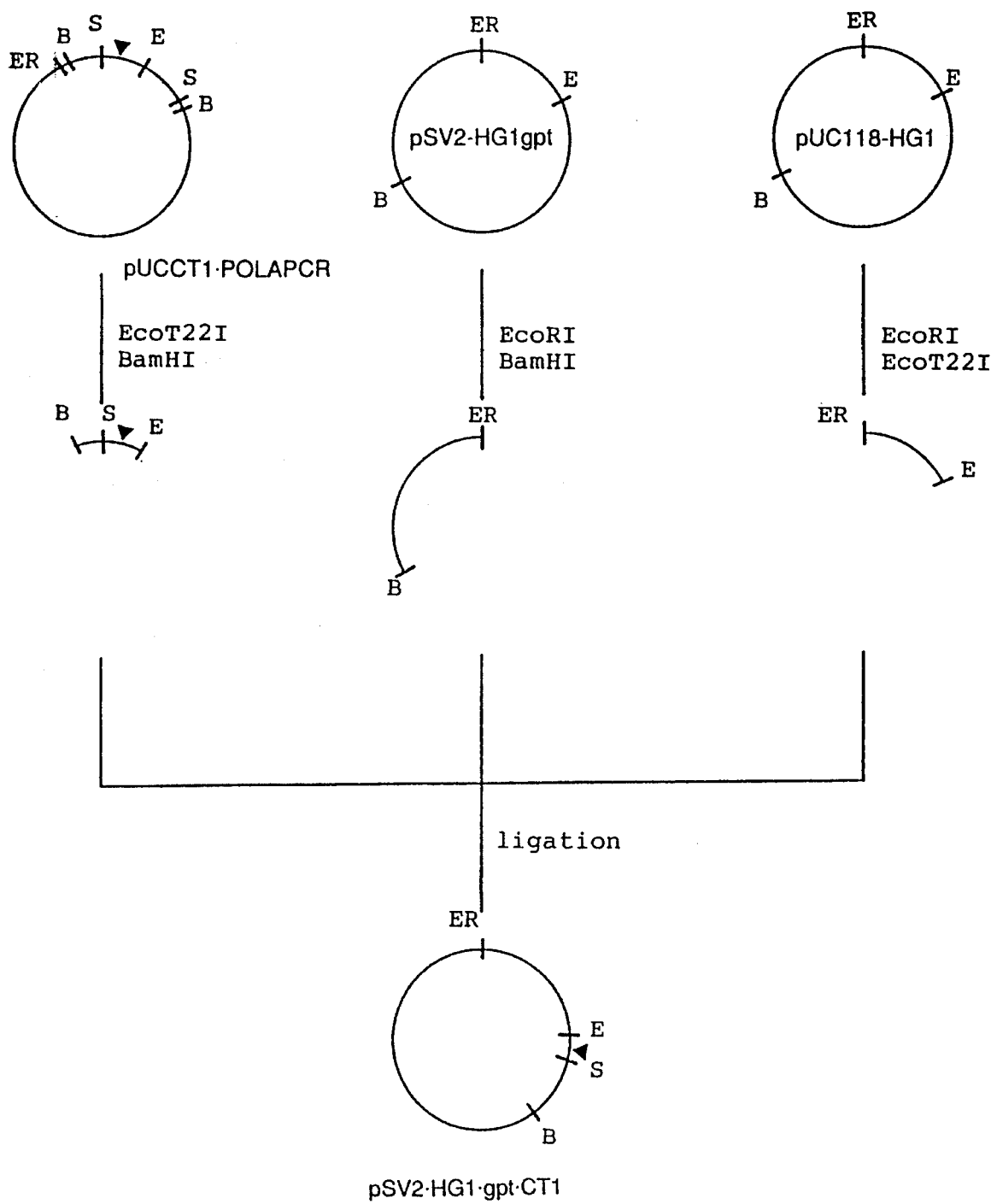
FIG. 6 shows the process of construction of the plasmid pSV2· HG1·gpt·CT1 and restriction map.

Next, 11.5 µg of the pSV2-HG1gpt described above was digested with 12 units of EcoRI and 12 units of BamHI in 30 µl of a reaction mixture containing buffer H for restriction enzyme reactions at 37° C. for 2 hours. The reaction mixture was treated by 1% agarose gel electrophoresis. The DNA fragment approximately 4.6 kbp long was obtained from the gel with use of DEAE-cellulose paper, and a DNA solution was obtained from the paper. The DNA fragment was purified from the DNA solution by phenol extraction and ethanol precipitation and dissolved in 50 µl of TE buffer. Then 4 µl Of the DNA fragment approximately 220 bp long prepared from pUCCT1·POLAPCR, 5 µl of the DNA fragment approximately 1750 bp long from pUC118-HG1, and 5 µl of the DNA fragment approximately 4.6 kbp long from pSV2-HG1gpt were allowed to react with 300 units of T4 DNA ligase in 20 µl of ligation buffer at 37° C. for 1 hour. A portion of the reaction mixture was used to transform E. coli HB101 cells. These transformed cells were spread over the surface of plates of LB agar containing 150 µg/ml ampicillin and incubated at 37° C. overnight. Single colonies of cells grown on the plates were inoculated into 2 ml of LB broth containing 150 µg/ml ampicillin and cultivated overnight at 37° C. with shaking at 230 rpm. Plasmids were extracted from these cultured cells and dissolved in 50 µl of TE buffer. Next, 3 µl of these plasmids were digested with 6 units of EcoRI, 6 units of EcoT22I, and 0.25 µg of RNase A in 10 µl of a reaction mixture containing buffer H for restriction enzyme reactions at 37° C. for 1 hour. The reaction mixtures were treated by 2% agarose gel electrophoresis and plasmids carrying a DNA fragment approximately 1.75 kbp long were selected. The PCR was performed with these plasmids as template DNA and with the primers used to prepare poly(A) fragment. A plasmid with which DNA fragment approximately 130 bp long was amplified was selected and named pSV2-HG1·gpt·CT1. The structure and restriction map of this plasmid are shown in FIG. 6.

Figure 7:
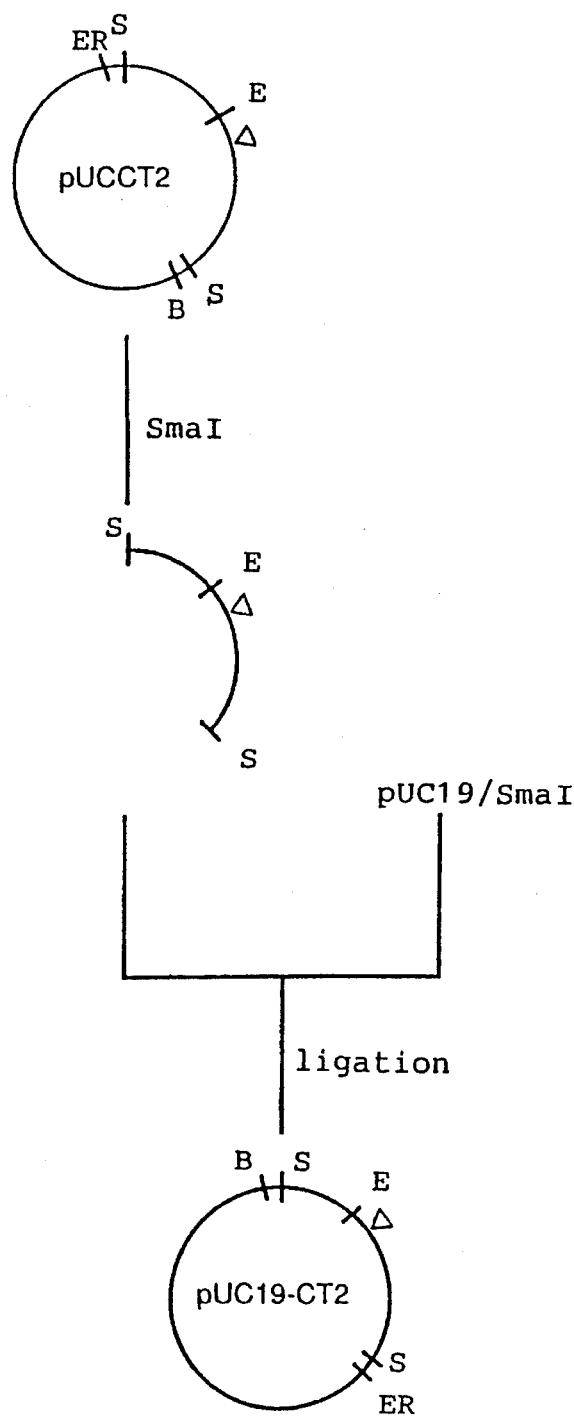
FIG. 7 shows the process of construction of the plasmid pUC19-CT2 and restriction map.
Figure 8:
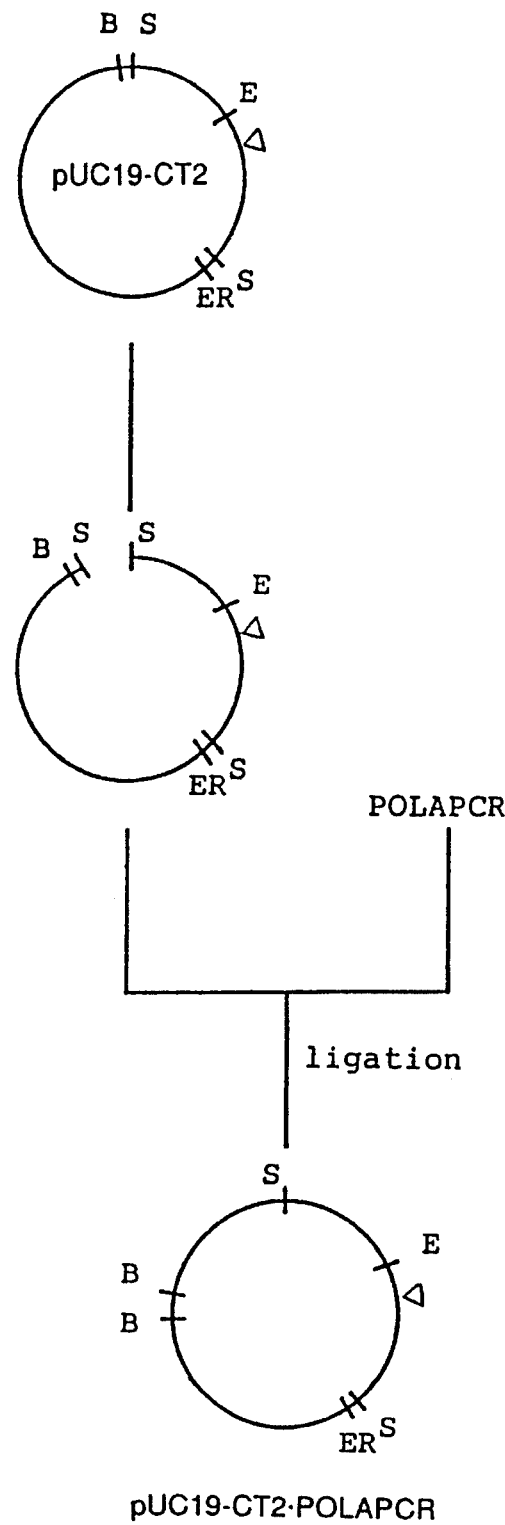
FIG. 8 shows the process of construction of the plasmid pUC19-CT2-POLAPCR and restriction map.

(ii) Next, 23.2 µg of pUCCT2 was digested with 20 units of SmaI in 302 µl of a reaction mixture containing buffer T for restriction enzyme reactions at 37° C. for 12 hours. The reaction mixture was treated by 8% polyacrylamide gel electrophoresis and a DNA fragment approximately 0.3 kbp long was purified. A portion of the DNA fragment and 1.5 µg of pUC19 digested with SmaI and dephosphorylated with E. coli alkaline phosphatase were allowed to react with 300 units of T4 DNA ligase in 60 µl of a reaction mixture containing ligation buffer at 37° C. 1 hr. A portion of the reaction mixture was used to transform E. coli HB101 cells. These transformed cells were spread over the surface of plates of LB agar plates containing 50 µg/ml ampicillin and incubated overnight at 37° C. Single colonies of cells grown on the plates were inoculated into 2 ml of LB broth containing 50 µg/ml ampicillin and cultivated overnight at 37° C. with shaking at 230 rpm. Plasmids were extracted from these cultured cells and dissolved in 50 µl of TE buffer. A portion of these plasmids was digested with 10 units of SmaI and 0.5 µg of RNase A in 15 µl of reaction mixtures containing buffer T for restriction enzyme reaction at 37° C. for 2 hours. The reaction mixtures were treated by 1% agarose gel electrophoresis and plasmids carrying a fragment approximately 0.3 kbp long were selected. A portion of these plasmids was digested with 6 units of EcoRI, 6 units of EcoT22I, and 0.5 µg of RNase A in 15 µl of a reaction mixture containing buffer H for restriction enzyme reactions at 37° C. for 2 hours. These reaction mixtures were treated by 6% polyacrylamide gel electrophoresis and the plasmid carrying a DNA fragment approximately 0.25 kbp long was selected. The plasmid was named pUCCT2. The structure and restriction map of the plasmid are shown in FIG. 7. In this and other figures, ▽ indicates the site at which DNA coding for the amino acid sequence of SEQ ID No.10 was inserted. First, 20 µg of pUC19-CT2 was allowed to react with 1 µg of RNase A in 52 µl of a reaction mixture containing buffer T for restriction enzyme reaction at 37° C. for 1 hour. Then, 7.5 units of SmaI was added to the reaction mixture and the DNA was partially digested with the enzyme. The reaction was started by addition of the enzyme, and 10-µl portions were sampled at 30, 60, 90, 150, and 210 seconds. The reaction was stopped by the mixture of each portion with phenol saturated with TE buffer. DNA was obtained by ethanol precipitation and dissolved in 50 µl of TE buffer. Then 2 µl of E. coli alkaline phosphatase was added to the DNA solution and incubated at 65° C. for 1 hour. The reaction mixture was treated by 1% agarose gel electrophoresis and a DNA fragment approximately 2 kbp long was obtained by electroelution. The eluted DNA fragment was purified with phenol extraction and ethanol precipitation. The DNA fragment purified was dissolved in 50 µl of TE buffer. Then 7 µl of the DNA solution and 8 µl of POLAPCR were allowed to react with 450 units of T4 DNA ligase in 60 µl of a reaction mixture containing ligation buffer at 37° C. for 1 hour. The reaction mixture was used to transform E. coli HB101 cells. The transformed cells were spread over the surface of plates of LB agar containing 50 µg/ml ampicillin. Single colonies of cells grown on the plates were inoculated into 2 ml of LB broth containing 50 µg/ml ampicillin and cultivated overnight at 37° C. with shaking at 230 rpm. Plasmids were extracted from these cultured cells and dissolved in 50 µl of TE buffer. Next, 11.5 µl of the plasmids was digested with 6 units of EcoRI, 6 units of BamHI, and 0.25 µg of RNase A in 15 µl of a reaction mixture containing buffer H for restriction enzyme reactions at 37° C. for 1 hour. The reaction mixtures were treated by 8% polyacrylamide gel electrophoresis and plasmids carrying a DNA fragment approximately 0.45 kbp long were selected. Then, 11.5 µl of these plasmids was digested with 6 units of BamHI and 0.25 μg of RNase A in 15 μl of a reaction mixture containing H-buffer H for restriction enzyme reactions at 37° C. for 1 hour. These reaction mixtures were treated by 8% polyacrylamide gel electrophoresis, and a plasmid carrying only a DNA fragment approximately 3.1 kbp was selected. The plasmid was named pUC19-CT2-POLAPCR. The structure and restriction map of this plasmid is shown in FIG. 8.

Next, 207 μg of pSV2-HG1gpt was digested with 30 units of SinaI in 103 μl of a reaction mixture containing buffer T for restriction enzyme reaction at 37° C. for 1 hour. The plasmid after the digestion was further digested with 36 units of BamHI in 206 μl of a reaction mixture containing buffer H for restriction enzyme reaction at 37° C. for 1 hour. The reaction mixture was treated by 8% agarose gel electrophoresis and a DNA fragment approximately 6.1 kbp long (fragment 1) was purified with use of DEAE-cellulose paper.

Next, 45 μl of pUC19-CT2 was digested with 20 units of SmaI in 52 μl of a reaction mixture containing buffer T for restriction enzyme reactions at 37° C. for 1 hour. Then, the reaction mixture was further treated with 24 units of EcoT22I and 0.5 μl of RNase A in 103 μl of a reaction mixture containing buffer H for restriction enzyme reaction at 37° C. for 1 hour. The reaction mixture was treated by 2% agarose gel electrophoresis and a DNA fragment approximately 0.2 kbp long (fragment 2) was purified. Next, 11.5 μl of pUC19-CT2-POLAPCR was digested with 24 units of BamHI, 24 units of EcoT22I, and 0.5 μg Of RNase A in 50 μl of a reaction mixture containing buffer H for restriction enzyme reactions at 37° C. for 1 hour. This reaction mixture was treated by 2% agarose gel electrophoresis and a DNA fragment approximately 0.21 kbp long (fragment 3) was purified.

Figure 9:
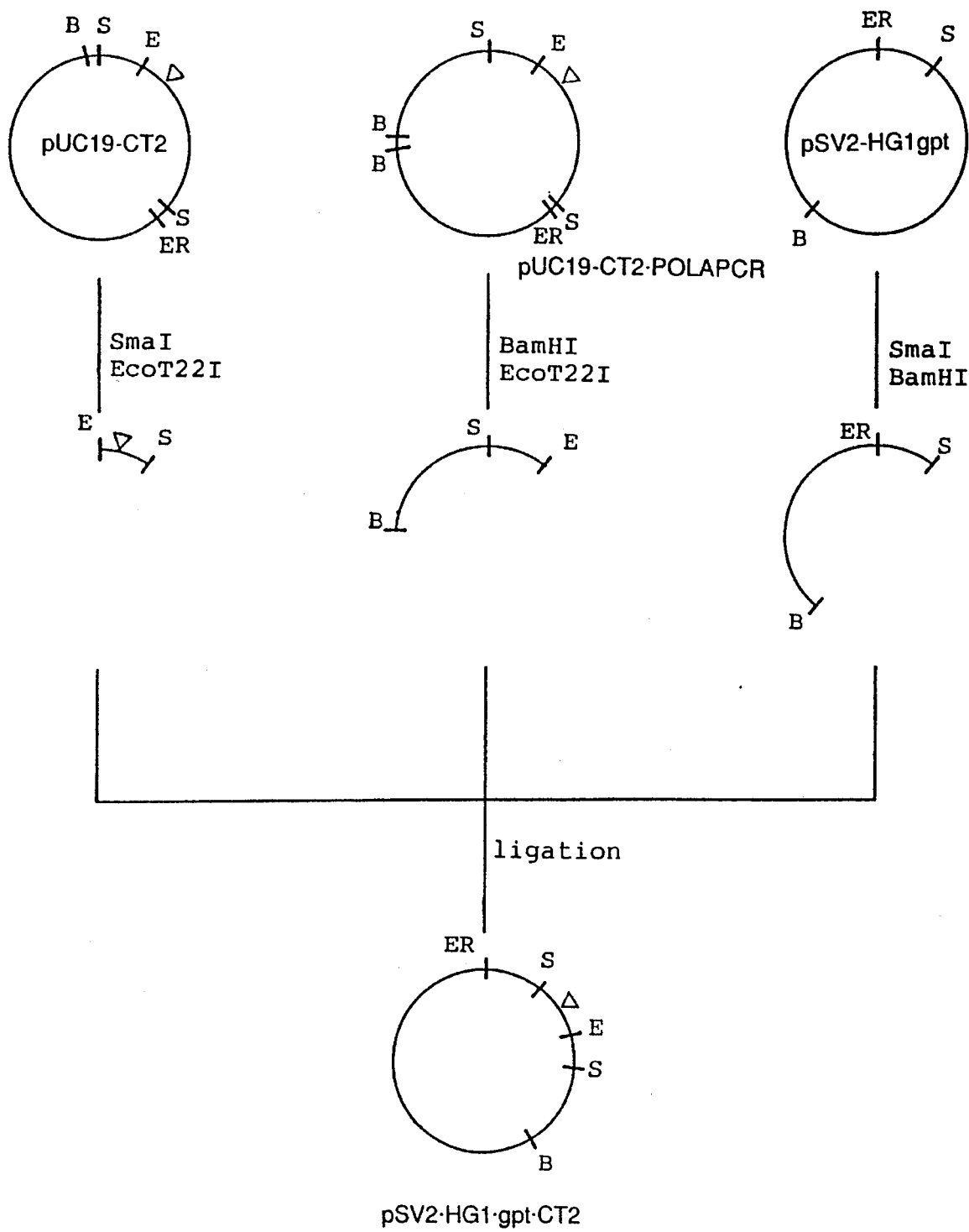
FIG. 9 shows the process of construction of the plasmid pSV2·HG1·gpt·CT2 and restriction map.

These fragments 1, 2, and 3 were allowed to react with 300 units of T4 DNA ligase in 21 μl of a reaction mixture containing ligation buffer at 37° C. for 1 hour. A portion of the reaction mixture was used to transform *E. coli* HB 101 cells. The transformed cells were spread over the surface of plates of LB agar containing 50 μg/ml ampicillin. Single colonies of cells grown on the plates were inoculated into 2 ml of LB broth containing 50 μg/ml ampicillin, and cultivated overnight at 37° C. with shaking at 230 rpm. Plasmids were extracted from the cultured cells and dissolved in 50 μl of TE buffer. Samples of these plasmids were digested with 6 units of EcoRI, 6 units of BamHI, and 0.5 μg of RNase A in 15 μl of a reaction mixture containing buffer H for restriction enzyme reactions at 37° C. for 90 minutes. The reaction mixture was treated by 0.8% agarose gel electrophoresis and a plasmid carrying DNA fragments approximately 4.6 kbp long and approximately 2.0 kbp long was selected. The plasmid was named pSV2-HG1-gpt-CT2. The structure and restriction map of the plasmid are shown in FIG. 9. This plasmid was used to transform *E. coli* HB101 cells. The transformed cells were named *Escherichia coli* HB101/CT2 and deposited at the Fermentation Research Institute of the Agency of Industrial Science and Technology 1-3, Higashi 1-chome, Tsukuba-shi Ibaraki-ken 305, Japan, as FERM BP-3399 on May 13, 1991.

By insertion of a DNA fragment coding for the variable region of IgG heavy chain into the plasmid pSV2-HG1-gpt-CT2 prepared from Escherichia coil HB101/CT2, mutagenized IgG heavy chains could be produced.

(5) Construction of mutagenized IgG expression vector

First, 15 μg of pSV2HG1Vpc, which carries a DNA fragment coding for the variable region of mouse IgG heavy chain of anti phosphorylcholine antibody and the constant region of human IgG heavy chain (gamma 1), was digested with 36 units of EcoRI in 100 μl of a reaction mixture containing buffer H for restriction enzyme reactions at 37° C. for 2 hours. This reaction mixture was treated by 1% agarose gel electrophoresis and a DNA fragment approximately 7.6 kbp long containing the region coding for the variable region of mouse IgG heavy chain of anti-phosphorylcholine antibody was obtained by use of DEAE-cellulose paper. The DNA obtained was purified by phenol extraction and ethanol precipitation, and dissolved in 50 μl of TE buffer. Next, 13.5 μg of the pSV2-HG1-gpt-CT1 described above was digested with 36 units of EcoRI in 53 μl of a reaction mixture containing buffer H for restriction enzyme reactions at 37° C. for 2 hours. Then, 1.2 units of *E. coli* alkaline phosphatase was added to the reaction mixture and the mixture was incubated at 65° C. for 1 hour. A DNA fragment was obtained from the reaction mixture with phenol extraction and ethanol precipitation and dissolved in 50μl of TE buffer.

Figure 10:
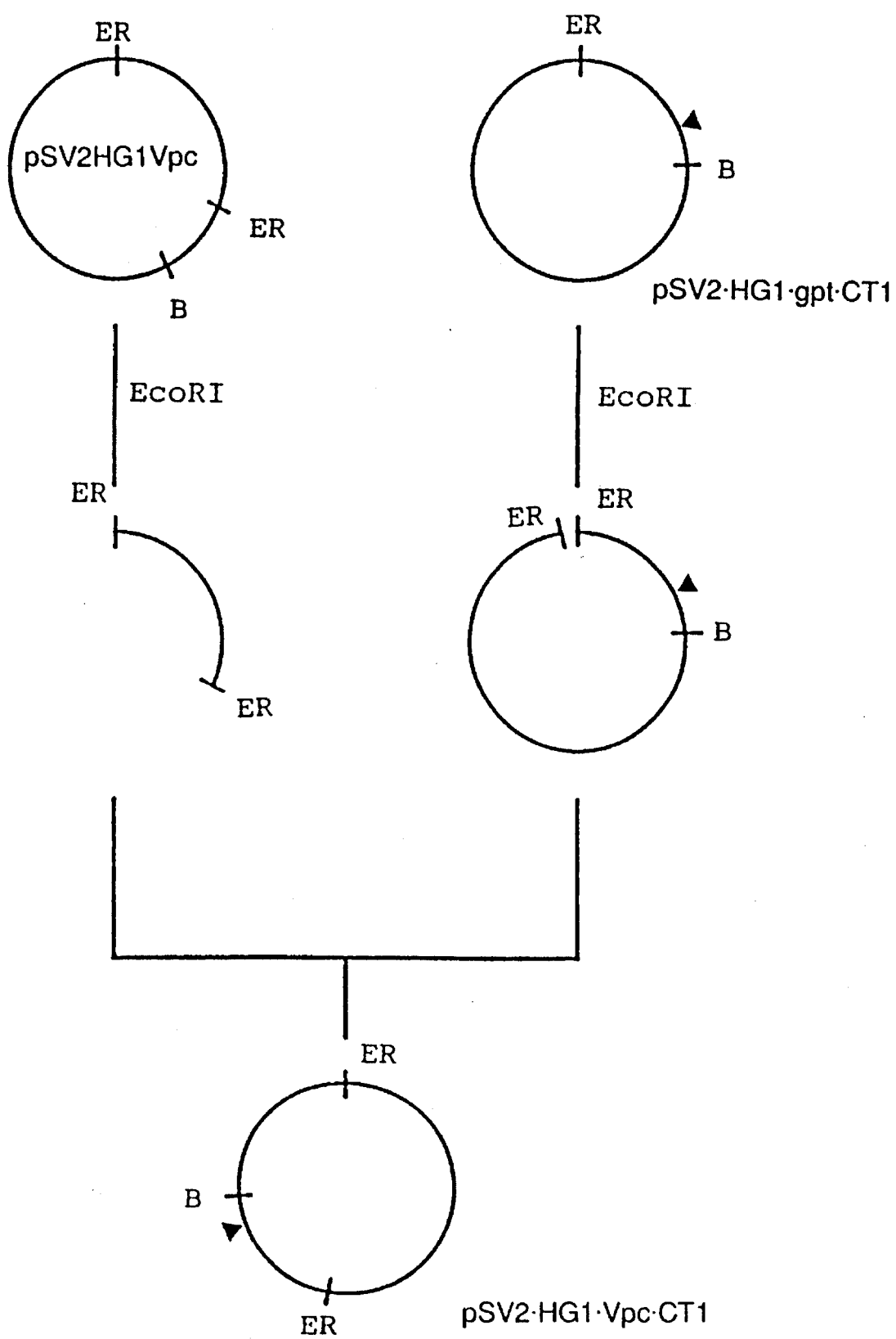
FIG. 10 shows the process of construction of the plasmid pSV2·HG1·Vpc·CT1 and restriction map.

Next, 5μl of the DNA fragment approximately 7.6 kbp long prepared from pSV2HG1Vpc and 3μl of pSV2-HG1-gpt-CT1 digested with EcoRI and dephosphorylated were mixed with 300 units of T4 DNA ligase in 20 μl of a reaction mixture containing ligation buffer and allowed to react at 37° C. for 1 hour. A portion of the reaction mixture was used to transform *E. coli* HB101 cells. The transformed cells were spread over the surface of plates of LB agar containing 50 μg/ml ampicillin and incubated overnight at 37° C. Single colonies of cells grown on the plates were inoculated into 2 ml of LB broth containing 50 μg/ml ampicillin and cultivated overnight at 37° C. with shaking at 230 rpm. Plasmids were extracted from the cultured cells and the plasmids were dissolved in 50 μl of TE buffer. Samples of the plasmids were digested with 6 units of EcoRI and 0.25 μg of RNase A in 10 μl of a reaction mixture containing buffer H for restriction enzyme reactions at 37° C. for 2 hours. The reaction mixtures were treated by 1% agarose gel electrophoresis, and plasmids carrying DNA fragments approximately 7.6 kbp long and approximately 6.6 kbp long were selected. A portion of the plasmids was digested with 12 units of StuI and 0.25 μg of RNase A in 10 μl Of a reaction mixture containing buffer H for restriction enzyme reactions at 37° C. for 2 hours. The reaction mixtures were treated by 1% agarose gel electrophoresis, and a plasmid carrying DNA fragments approximately 6.3 kbp long, approximately 5.4 kbp long, and approximately 2.5 kbp long was selected. The plasmid was named pSV2-HG1-Vpc-CT1. The structure and restriction map of the plasmid are shown in FIG. 10.

Figure 11:
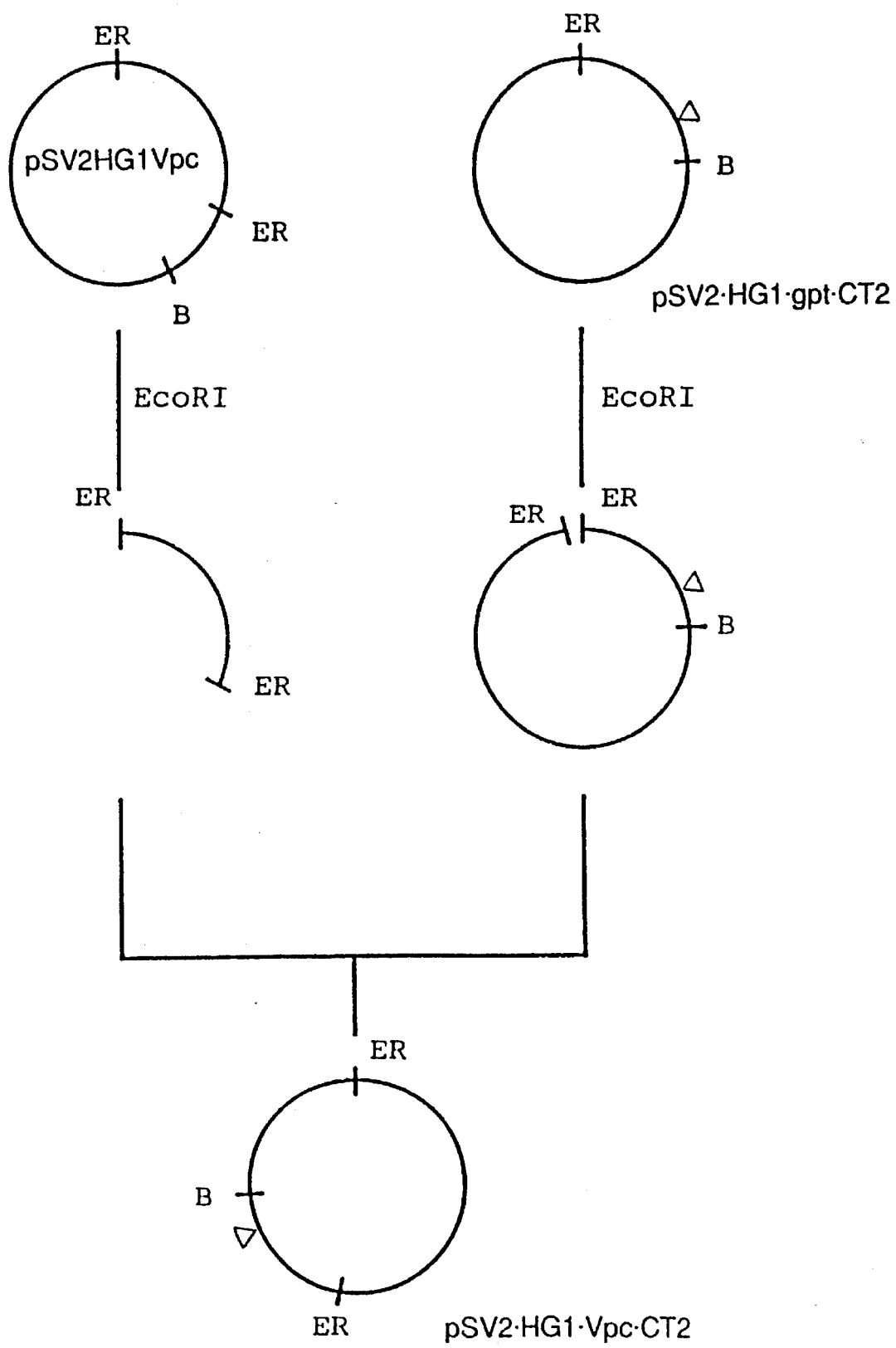
FIG. 11 shows the process of construction of the plasmid pSV2·HG1·Vpc·CT2 and restriction map.

Next, by the method described above, another plasmid carrying the region coding for the variable region of the IgG heavy chain and also the region coding for the constant region of the IgG heavy chain, which constant region contained an introduced R-S sequence, was constructed by insertion of a DNA fragment prepared from a digest of pSV2HG1Vpc with EcoRI into the digest of pSV2-HG1-gpt-CT2 with EcoRI. The plasmid that was constructed was named pSV2-HG1-Vpc-CT2. The structure and restriction map of this plasmid are shown in FIG. 11.

EXAMPLE 2

Production and purification of IgG containing the introduced R-S sequence.

(1) Transfection of mouse myeloma cell SP2/O

Mouse myeloma SP2/O cells were grown in RPMI 1640 medium supplemented with 10% fetal calf serum, 50 units/ ml penicillin, and 50 µg/ml streptomycin (basal medium). The cells were harvested from 100 ml of the culture with centrifugation for 10 minutes at 1000 rpm and 4° C. The harvested cells were suspended in 10 ml of ice-cold phosphate-buffered saline(PBS; 8 g/l NaCl, 0.2 g/l KCl, and 1.15 g/l $Na_2HPO_4$) and centrifuged for 10 minutes at 1000 rpm and 4° C. A pellet of cells was resuspended in 10 ml of ice-cold PBS and centrifuged for 10 minutes at 1000 rpm and 4° C. The collected cells were suspended in 1 ml of ice-cold plasmid solution containing 50 µg of pSV2·HG1·Vpc·CT1 and 50 µg of pSV2CκVpc. The cell suspension was transferred in a cuvette for electroporation and incubated on ice for 10 minutes. The cuvette containing cells and DNAs was pulsed three times at 4500 V/cm for 50 µsec and then returned to the ice and incubated for an additional 10 minutes each time. The suspension was added to 20 ml of basal medium and incubated at 37° C. under 5% $CO_2$ in a $CO_2$ incubator for 3 days. Then, the cultured cells were suspended in 10 ml of selection medium that contained 250 µg/ml xanthine and 10 µg/ml mycophenolic acid, and placed into a 96-well culture dish at the volume of 100 µl/well. In a control experiment, mouse myeloma SP2/O cells were transfected with the pSV2HG1Vpc and pSV2CκVpc described above.

(2) Selection of a positive clone.

A monoclonal antibody to mouse Fab fragment was adjusted to the concentration of 10 µg/ml with PBS, and 50 µl of the solution was added into each well of a 96-well titer plate and incubated at room temperature for 2 hours, after which the solution was removed from the wells. Next, 400 µl of 1% bovine serum albumin was added to each well and the plates were incubated at room temperature for 1 hour. Then, the wells were washed with PBS containing 0.05% Tween 20, and 50 µl of the culture supernatant was added to the wells and incubated at room temperature for 1 hour. After the incubation, the wells were washed with PBS containing 0.05% Tween 20. Then 50 µl of antibody to human IgG Fc fragment conjugated with horseradish peroxidase (POD) was added to each well, and the plate was incubated at room temperature for 1 hour. After the incubation, the wells were washed with PBS containing 0.05% Tween 20. Next, 50 µl of peroxide-o-phenylenediamine solution was added to each well and the plate was incubated at room temperature for 20 minutes, after which 50 µl of 1 M $H_2SO_4$ was added to each well. The absorbance of the reaction mixtures was measured at 492 nm and positive clones were selected. The clone that produced the most amount of IgG was selected, named Myeloma SP2-PCCT1, and deposited at the Fermentation Research Institute of the Agency of Industrial Science and Technology, Japan, as FERM P-11547.

(3) By procedures described in example 2-(1), (2)

Mouse myeloma SP2/O cells were transformed with pSV2·HG1·Vpc·CT2 and pSV2CκVpc. The clone that produced the most amount of IgG was selected and named Myeloma SP2-PCCT2 and deposited at the Fermentation Research Institute of the Agency of Industrial Science and Technology, Japan, as FERM BP-3390.

(4) Purification of IgG.

Myeroma SP-PCCT1 (FERM P-11547) and Myeloma SP2-PCCT2 (FERM BP-3390) were separately cultured in selection medium that is RPMI 1640 medium supplemented with 10% fetal calf serum, 50 units/ml penicillin, 50 µg/ml streptomycin, 250 µg xanthine, and 10 µg/ml mycophenolic acid. From each culture, 500 ml of each supernatant was obtained. From the supernatants, IgGs were purified with Immuno Pure IgG Purification Kit (Pierce, Rockford, Ill.), and 100 µg of IgG was obtained. IgG purified from the supernatant of Myeloma SP2-PCCT1 was named CT1, that from Myeloma SP2-PCCT2 was named CT2. From the culture of control cells, 100 µg of control IgG was purified.

EXAMPLE 3

Assay of cell adhesion

CT1 and CT2, which were human-mouse chimera IgG containing an introduced R-S sequence, control IgG and human plasma fibronectin were assayed for cell adhesive activity toward fibroblast cells of baby hamster kidney (BHK). The sample to be tested was dissolved in PBS. Then 50 µl of sample was added in each well of a 96-well microtiter plate, which was incubated at 4° C. overnight to allow the sample to adsorb to the wells. The wells were washed with PBS. Next, 100 µl of 1% bovine serum albumin (BSA) was added to each well and the plate was incubated at room temperature for 3 to 4 hours. Then, the plate was washed with PBS and used in the assay of cell adhesion.

BHK cells grown in Dulbecco's modified Eagle (DME) medium supplemented with 10% fetal calf serum, 50 units/ml penicillin, and 50 µg/ml streptomycin were detached by incubation at 37° C. for 2 min in PBS containing 0.25% trypsin and 0.02% EDTA. These detached cells were suspended in ice-cold DME/HEPES buffered saline (1:1) and collected by centrifugation at 800 rpm for 4 minutes. The collected cells were suspended in ice-cold DME/HEPES saline containing 0.1% soybean trypsin inhibitor and centrifuged at 800 rpm for 4 minutes. The collected cells were suspended in ice-cold DME/HEPES buffered saline and centrifuged at 800 rpm for 4 minutes. The collected cells were suspended in ice cold DME medium not supplemented with fetal calf serum and the cell concentration was adjusted to $5 \times 10^5$–$1 \times 10^6$/ml. Then 50 µl of cell suspension was added to each well coated with sample. The cells were incubated at 37° C. for 1 hour in a $CO_2$ incubator and then non-attached cells were removed by washing of the plate. Attached cells were fixed on the plate with 4% formaldehyde and observed under a microscope. IgGs containing the introduced R-S sequence were capable of mediating cell adhesion, and IgG not containing the R-S sequence was inactive.

Example 4

Assay of binding activity to antigen.

(1) Preparation of antigen.

To assay the antigen binding activity of mutagenized IgGs, phosphorylcholine bound to keyhole limpet hemocyanin (PC-KLH) was prepared. To do this, 30 mg of p-aminophenylphosphorylcholine was dissolved in 1.5 ml of 0.2 N HCl, and 0.2 M sodium nitrite was added dropwise into the solution for 1 hour until there was an excess. In this example, approximately 500 µl of 0.2 M sodium nitrite was added, and the amount was confirmed to be an excess amount by the use of potassium iodide starch paper. Then, 1.26 ml of the solution was dropped into 5 ml of KLH solution (11.2mg of KLH in 70 mM sodium borate, pH 9.0, and 80 mM NaCl) over 10 min at room temperature. The mixture was incubated at 4° C. for 17 hr with gently stirring. After incubation, by dialysis of the mixture against PBS, PC-KLH solution was obtained.

(2) Assay for antigen binding

PC-KLH was used to coat the wells of a 96-well microtiter plate by addition of 50 ml of PC-KLH solution (100 μg/ml) to each well, and the plate incubated at room temperature for 1 hour. After incubation, the plate was washed with PBS containing 0.1% Tween 20 to remove non-absorbed PC-KLH. After the washing, to block the surface of well, 100 μl of PBS containing 1% BSA was added to each well and the plate was incubated at room temperature for 1 hour. After the incubation, the plate was washed with PBS containing 0.1% Tween 20, and 50 μl of a mutagenized IgG (CT1 or CT2) or of control IgG was added to each well and the plate was incubated at room temperature for 1 hour. After incubation, the plate was washed with PBS containing 0.1% Tween 20. Next, 50 μl of antibody to human IgG Fc fragment conjugated with POD conjugate was added to each well and the plate was incubated at room temperature for 1 hour. After incubation, the plate was washed with PBS containing 0.1% Tween 20. Then 50 μl of $H_2O_2$-o-phenylenediamine solution was added to each well and the plate was incubated at room temperature for 20 min. Next, 100 μl of 1 M $H_2SO_4$ was added to each well. The absorbance of the reaction mixture at 492 nm was measured to find the binding activity of these IgGs to PC-KLH. These results suggested that the mutagenized IgGs, CT1 and CT2, had binding activity to antigen that was as strong as that of control IgG. Results of Examples 3 and 4 are shown in Table 1.

TABLE 1

| sample | | cell-adhesive activity | antigen-binding activity |
|---|---|---|---|
| FN | | +++ | |
| IgG containing introduced R-S sequence | CT1 | + | + |
| | CT2 | ++ | + |
| Control IgG | | — | + |

As explained above, according to this invention, it is possible to provide antibodies that have strengthened affinity for cells by the artificial introduction of cell-adhesive activity. These multifunctional antibodies can accelerate the phagocytosis of macrophages and activate other effector cells. So, these multifunctional antibodies are of use in the self-defense mechanism of organisms that involves antibodies and effector cells. In addition, the movement of the antibodies to the tissue is increased, so the effects of the antibodies are increased in the tissues, as well.

What we claim is:

1. An isolated DNA coding for a constant region of a human immunoglobulin IgG H-chain polypeptide which contains an RGDS amino acid sequence and has cell adhesive activity, wherein said DNA has the sequence of SEQ. ID. No. 4 and is obtained from *Escherichia coli* HB 101/CT2 (FERM BP-3399).

2. An isolated DNA coding for a constant region of a human immunoglobulin IgG H-chain polypeptide which contains an RGDS amino acid sequence and has cell adhesive activity, wherein said DNA has the sequence of SEQ. ID. No. 4.

* * * * *